(12) United States Patent
Kitto et al.

(10) Patent No.: US 7,189,402 B1
(45) Date of Patent: Mar. 13, 2007

(54) LIVE VACCINE FOR HUMAN IMMUNODEFICIENCY VIRUS

(75) Inventors: George Barrie Kitto, Austin, TX (US); Mary Susan Burnett, Fairfax, VA (US)

(73) Assignee: Research Development Foundation, Carson City, NV (US)

( * ) Notice: Subject to any disclaimer, the term of this patent is extended or adjusted under 35 U.S.C. 154(b) by 398 days.

(21) Appl. No.: 09/244,195

(22) Filed: Feb. 4, 1999

Related U.S. Application Data

(60) Provisional application No. 60/073,943, filed on Feb. 6, 1998.

(51) Int. Cl.
*A61K 39/02* (2006.01)
*A61K 39/295* (2006.01)

(52) U.S. Cl. .................... 424/200.1; 424/208.1

(58) Field of Classification Search ............ 424/188.1, 424/208.1, 192.1, 200.1; 435/69.7
See application file for complete search history.

(56) References Cited

U.S. PATENT DOCUMENTS

| | | | | | |
|---|---|---|---|---|---|
| 4,981,790 | A | * | 1/1991 | Haseltine et al. | 435/69.1 |
| 5,112,749 | A | * | 5/1992 | Brey et al. | 435/172.3 |
| 5,194,376 | A | * | 3/1993 | Kang | 435/69.1 |
| 5,202,259 | A | * | 4/1993 | Goff et al. | 435/252.33 |
| 5,288,623 | A | * | 2/1994 | Zenno et al. | 435/69.7 |
| 5,348,867 | A | * | 9/1994 | Georgiou et al. | 435/69.7 |
| 5,606,026 | A | * | 2/1997 | Rodman | 530/387.9 |

OTHER PUBLICATIONS

Haynes, B., 1993, "Scientific and social issues of human immunodeficiency virus vaccine development", Science 260:1279-1286.*

Graham, B. and P. Wright, 1995, "Candidate AIDS vaccines.", New Engl. J. Med. 333(20):1331-1339.*

Haynes, B., et al., 1996, "Update on the issues of HIV vaccine development.", Ann. Med. 28:39-41.*

Lee, T.-H., 1997, "Acquired immunodeficiency disease vaccines: design and development.", in *AIDS: Biology, Diagnosis, Treatment and Prevention, fourth edition,* DeVita, Jr., V, et al., eds., Lippincott-Raven Publishers, pp. 605-616.*

Hone, D.M., et al., 1996, Optimization of live oral *Salmonella*HIV-1 vaccine vectors for the induction of HIV-specific mucosal and systemic immune responses. J. Biotech. 44:203-207.*

Thimmig, R.L. and C.S. McHenry, 1993, Human immunodeficiency virus reverse transcriptase. J. Biol. Chem. 268(22):16528-16536.*

Hone, D.M., et al., 1996, Optimization of live oral *Salmonella*-HIV-1 vaccine vectors for the induction of HIV-specific mucosal and systemic immune responses. J. Biotech. 44:203-207.*

Thimmig, R. L., et al. Aug. 1993. Human immunodeficiency virus reverse transcriptase. J. Biol. Chem. 268(22):16528-16536.*

\* cited by examiner

*Primary Examiner*—J. S. Parkin
(74) *Attorney, Agent, or Firm*—Fulbright & Jaworski L.L.P.

(57) ABSTRACT

The present invention discloses development of a model live vaccine for HIV, using an attenuated strain of *Salmonella* engineered to surface express specific HIV proteins and testing of this vaccine in mice. There are provided two recombinant plasmids, containing the Lpp-OmpA genes required for surface exposure, followed by the genes for the HIV-1 proteins, Reverse Transcriptase or Transactivating protein (Tat). These plasmids are electroporated into an attenuated strain of *Salmonella*, and antigen expression is verified. These live vaccines are then used to orally inoculate mice and the vaccinated mice are tested for fecal IgA response and helper T cell response specific for the HIV antigens.

6 Claims, 14 Drawing Sheets

LIVE VACCINE FOR HUMAN IMMUNODEFICIENCY VIRUS

CROSS-REFERENCE TO RELATED APPLICATION

This application claims priority to U.S. Ser. No. 60/073,943, filed Feb. 6, 1998, now abandoned.

FEDERAL FUNDING NOTICE

The present invention was funded in part by an NIH Biotechnology Training Grant. Consequently, the United States government has certain rights in this invention.

BACKGROUND OF THE INVENTION

1. Field of the Invention

The present invention relates generally to the field of molecular biology and biochemistry. More specifically, the present invention relates to development of a live vaccine for human immunodeficiency virus (HIV).

2. Description of the Related Art

Vaccines are a most cost-effective treatment of infectious diseases. Successful vaccines have greatly reduced the incidence of measles, mumps, pertussis, rubella, poliomyelitis, tetanus, and small pox. The development of an effective vaccine for HIV is imperative. Estimates from the World Health Organization predict that by the year 2000, 40 million people will be infected with HIV world wide.

A recent evaluation of HIV vaccine development approaches is described by Schultz in *Changing Paradigms for an HIV Vaccine* (Schultz, 1996). In this article Schultz discusses several paradigms, the first of which is calls "sterilizing immunity". It was originally believed that in order to prevent AIDS, HIV infection must be completely prevented. The logical method for accomplishing such a goal was to induce high titers of neutralizing antibodies. The only legitimate antigens for such a vaccine are gp120 and gp41, the HIV envelope proteins, which contain neutralizing epitopes. Several general methods were used for developing these vaccines. First, genetically engineered expression systems were used to produce the envelope subunit proteins, gp120 or gp160. The recombinant proteins were then formulated into alum or in novel adjuvants. The second method involved inserting HIV env genes into live vectors such as vaccinia and canarypox. The third approach used peptide epitopes, in an attempt to eliminate irrelevant epitopes, thereby forcing the immune system to focus on the relevant, neutralizing epitopes.

Two additional series of experiments falling under the "sterilizing immunity" paradigm involves research done in non-human primates. Whole-inactivated vaccines are very common and have been very effective. With HIV however, no such study has ever been attempted in humans, primarily due to the grave consequences if viral particles were ever not completely inactivated.

The second paradigm for HIV vaccine development involves concepts not new to vaccine research, but represents a change in approach for dealing with HIV. Rather than initial prevention of infection, an infection begins, but is contained and eventually cleared. A vaccine may be deemed effective if the viral load is rapidly cleared, or reduced to such a level that it no longer produces symptoms, or permits transmission to others (Johnston, 1997). One of the main developments that led to this change in perspective is the fact that blood AIDS virus levels indicate a steady-state balance between daily production and clearance of enormous amounts of HIV (Wei, 1995, Ho, 1995). These findings illustrate that the immune system is nearly successful in defeating the virus but after time finally succumbs to HIV.

Some current research on the HIV virus includes the use of gag gene, protease genes, and parts of the pol gene. Additional work focuses on using pseudovirions, which are a non-infectious and safe form of whole-inactivated virus. One such vaccine is currently in small primate trials. Synthetic peptide vaccines have also been explored and found to induce a cytotoxic T lymphocyte response in mice if conjugated to certain lipid moieties. Human testing is currently underway on some of these peptide products. DNA based vaccines are also being explored, as they are relatively inexpensive and easily produced. Early results indicate good cellular response, as well as strong humoral immunity (Glaser, 1997).

The majority of HIV infections are transmitted via mucosal surfaces. This route of entry strongly suggests that a vigorous mucosal immune response would be desirable. It has traditionally been difficult to elicit such responses at the mucosal surface. Recent work presented at the 9th Annual Meeting of the National Cooperative Vaccine Development Groups for AIDS (May, 1997) by Musey, described the presence of HIV specific cytotoxic T lymphocytes in the mucosa of the genital tract in infected men and women. Mucosal T cells were isolated from male semen samples and female cervical brushings and stimulated with different specific antigens from HIV. Responses were seen to the HIV Env, Gag and Pol proteins. Additional research presented at the same Meeting (May 1997) by Clerici, points to possible protection of uninfected partners by mucosal IgA.

Developing a live vaccine has several advantages over developing a dead vaccine (subunit vaccine). Attenuated strains of bacteria have been genetically manipulated to express virulence antigens from different pathogens. It has been found that several of these bacteria are capable of eliciting both humoral and cellular immune responses not only against the wild type of their species, but also against the pathogen providing the genetic material for the antigen (Curtiss, 1989).

Strains of *Salmonella* have the ability to bind preferentially to M cells in the intestinal mucosa. While this tactic would normally allow the immune system to mount a response and clear the infection, *Salmonella* have developed a unique way of evading detection. Once in the mucosa, *Salmonella* are actually taken up into cells in endosomes, and can remain there undetected. Bacteria have been captured on film dividing inside such endosomes in human cell lines (Sztein, 1995). This adaptation of *Salmonella* may prove to be very helpful in developing a vaccine. If enough of the attenuated *Salmonella* can survive inside cells, perhaps this can aid in the establishment of a long-term infection, and result in lasting immunity to the foreign antigens.

Another major benefit of using *Salmonella* is that the bacteria seem to serve as an adjuvant, resulting in a greater immune response than if the antigen were administered alone. Subunit vaccines, administered alone, often elicit weaker responses, and there are currently few adjuvants that are available for use in humans. Even with the aid of adjuvants, the parenteral delivery of most subunit vaccines fails to induce a secretory response at the mucosal surface, or stimulate a strong T cell response. As mentioned previously, both a strong cell mediated response and mucosal immunity are believed to be important in possibly clearing an HIV infection.

The prior art is deficient in an inexpensive live vaccine for human immunodeficiency virus. The present invention fulfills this long-standing need and desire in the art.

SUMMARY OF THE INVENTION

The present invention discloses development of a model live vaccine for HIV, using an attenuated strain of *Salmonella* engineered to surface express specific HIV proteins. In one embodiment, there is provided a live vaccine for human immunodeficiency virus comprising a recombinant plasmid containing genes required for surface exposure and a gene encoding a human immunodeficiency virus protein.

In one embodiment of the present invention, there are provided recombinant plasmids, containing the Lpp-OmpA genes required for surface exposure, followed by the genes for the HIV-1 proteins, Reverse Transcriptase, or Transactivating protein (Tat). In a preferred embodiment, the plasmids are electroporated into an attenuated strain of *Salmonella*, SL3261.

In another embodiment of the present invention, the live vaccines are used to orally inoculate mice and said animals are then tested for fecal IgA response and helper T cell responses specific for the HIV antigens.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
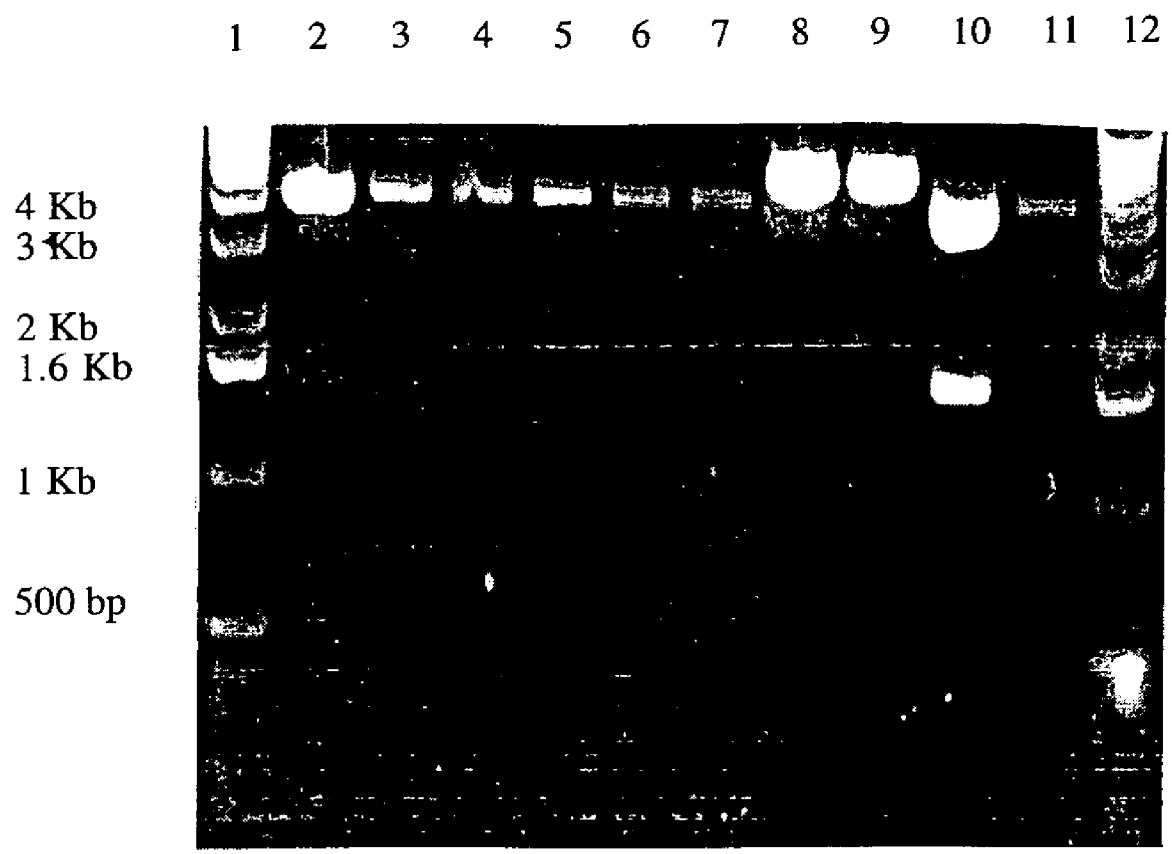
FIG. 1 shows colony screening for the recombinant plasmid pHART. Lanes 1 and 12 contain molecular weight standards. Lanes 2–11 contain plasmids digested with HindIII.
Figure 2:
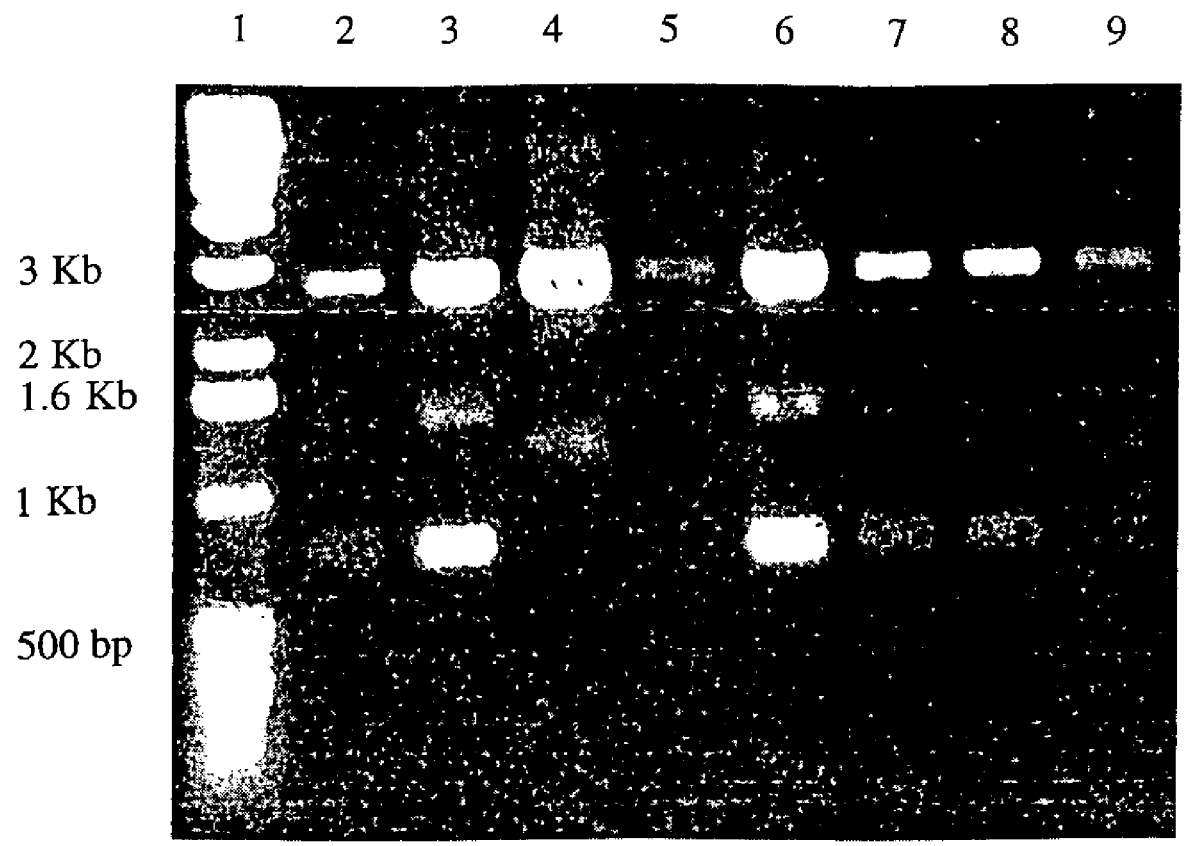
FIG. 2 shows colony screening for recombinant pHAT. Lane 1 contains the molecular weight standard. Remaining Lanes contain plasmids digested with HindIII.
Figure 3:
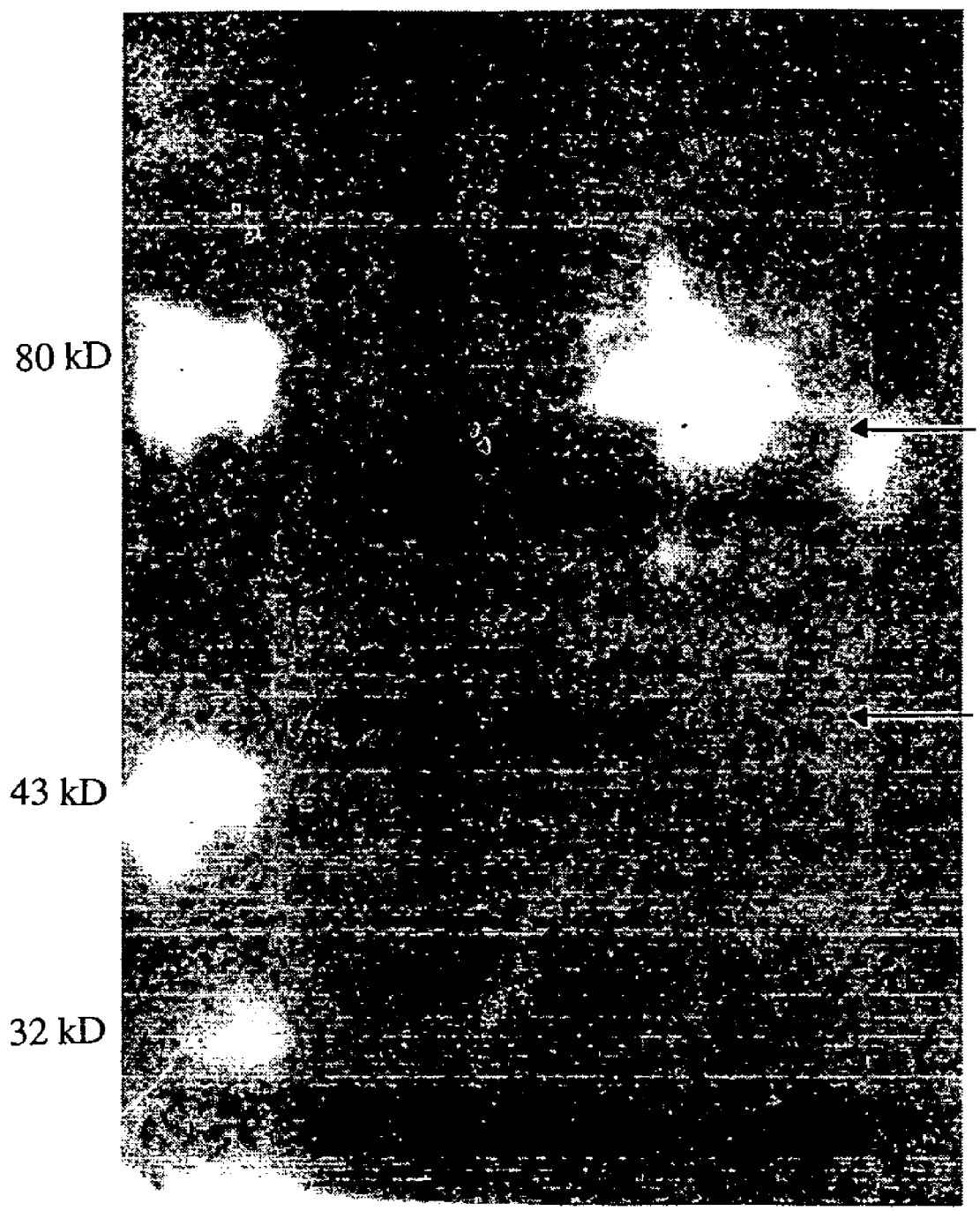
FIG. 3 shows western blot of *E. coli* DH5α-pHART. Lane 1 contains molecular weight standards. Lanes 2, 3 and 4 are whole cell lysates of induced *E. coli* DH5α-pHART, uninduced *E. coli* DH5α-pHART and control *E. coli* DH5α, respectively. Unique bands in lanes 2 and 3 are indicated with arrows.
Figure 4:
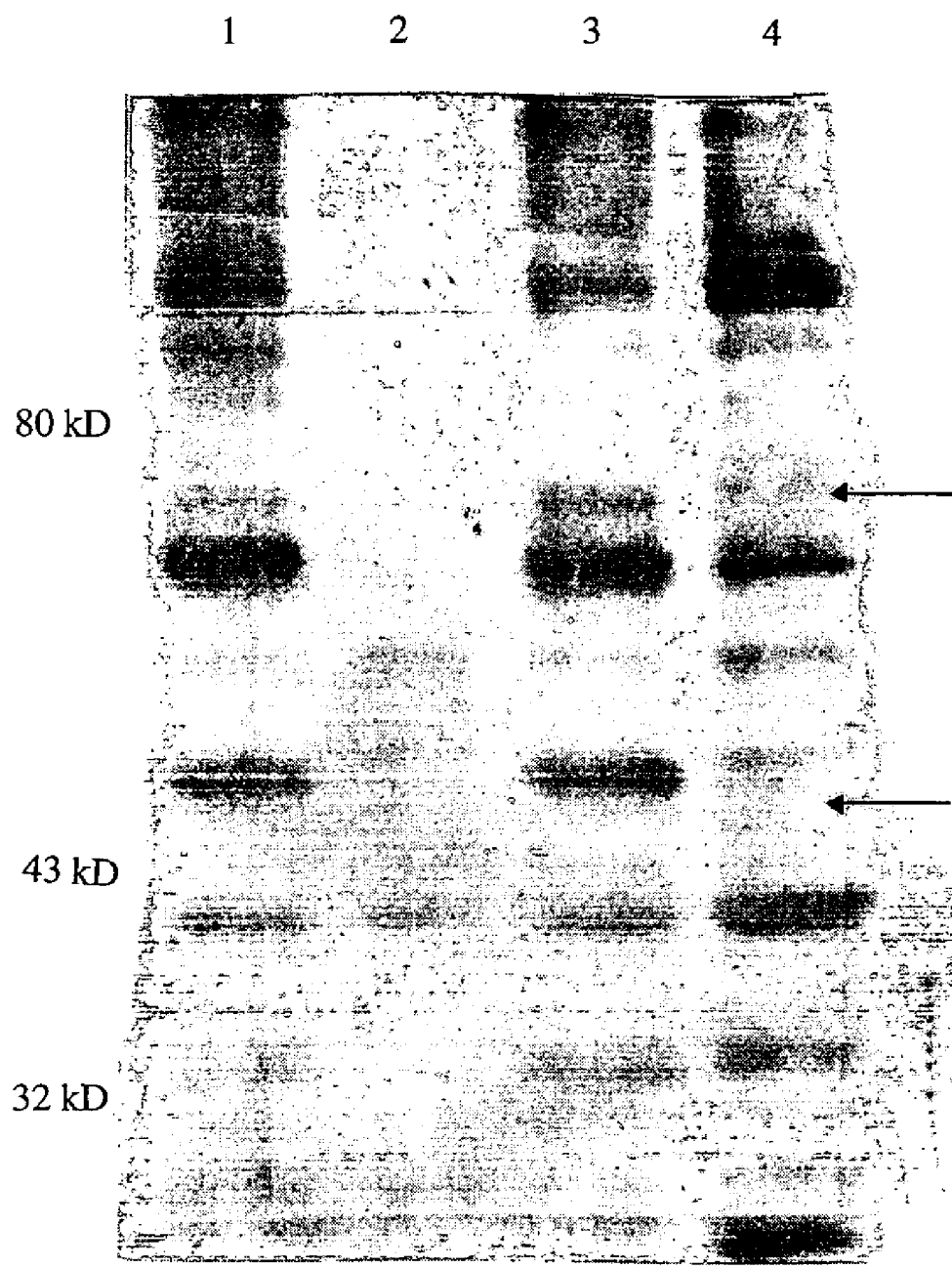
FIG. 4 shows western blot of *E. coli* DH5α-pHART crude membrane preparations. Lanes 1 and 2 are the outer membrane fraction of *E. coli* DH5α-pHART and of control *E. coli* DH5α, respectively. Lanes 3 and 4 are the whole membrane fraction of *E. coli* DH5α-pHART and of control *E. coli* DH5α, respectively. Unique bands in lanes 1 and 3 are indicated with arrows.
Figure 5:
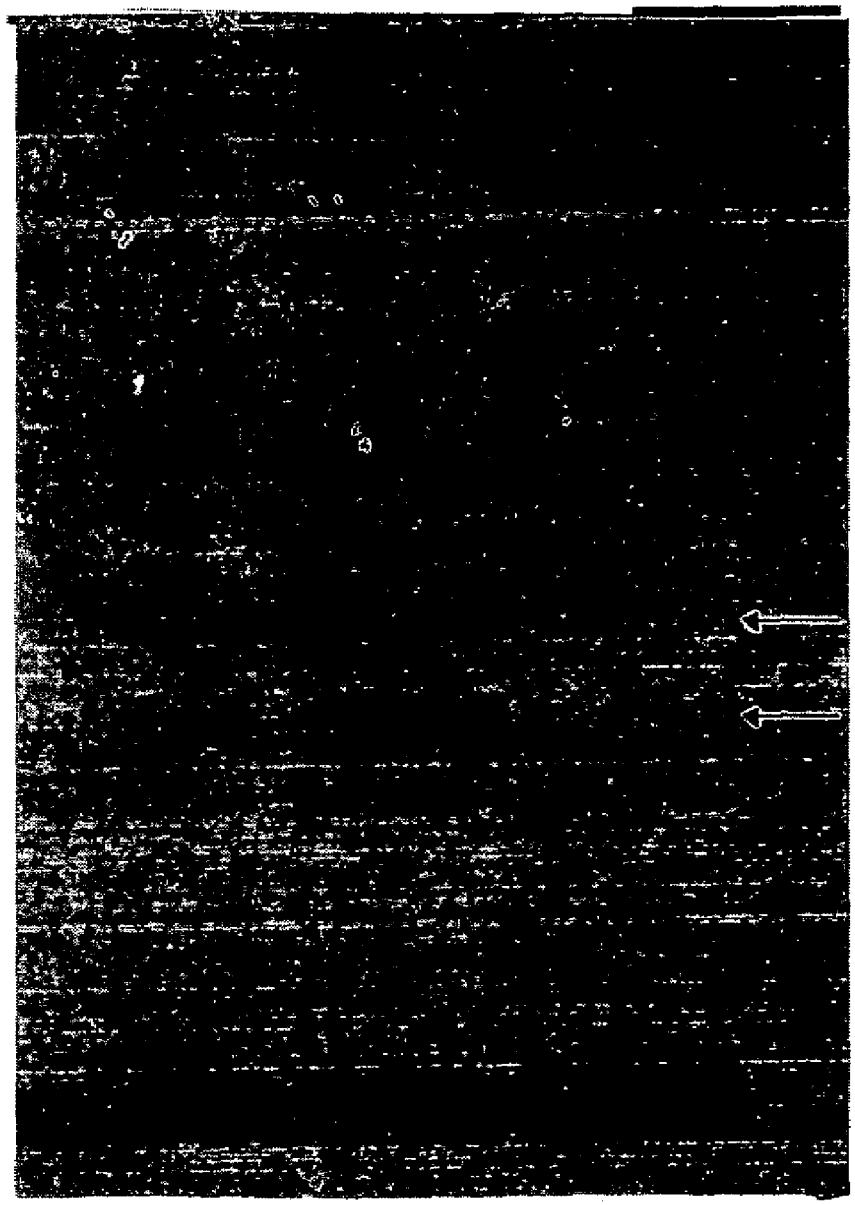
FIG. 5 shows western blot of *E. coli* DH5α-pHAT. Lanes 1, 2 and 3 contain the whole cell lysate of induced E. coli DH5α-pHAT, uninduced *E. coli* DH5α-pHAT and control *E. coli* DH5α, respectively. Unique bands in lanes 1 and 2 are indicated with arrows.
Figure 6:
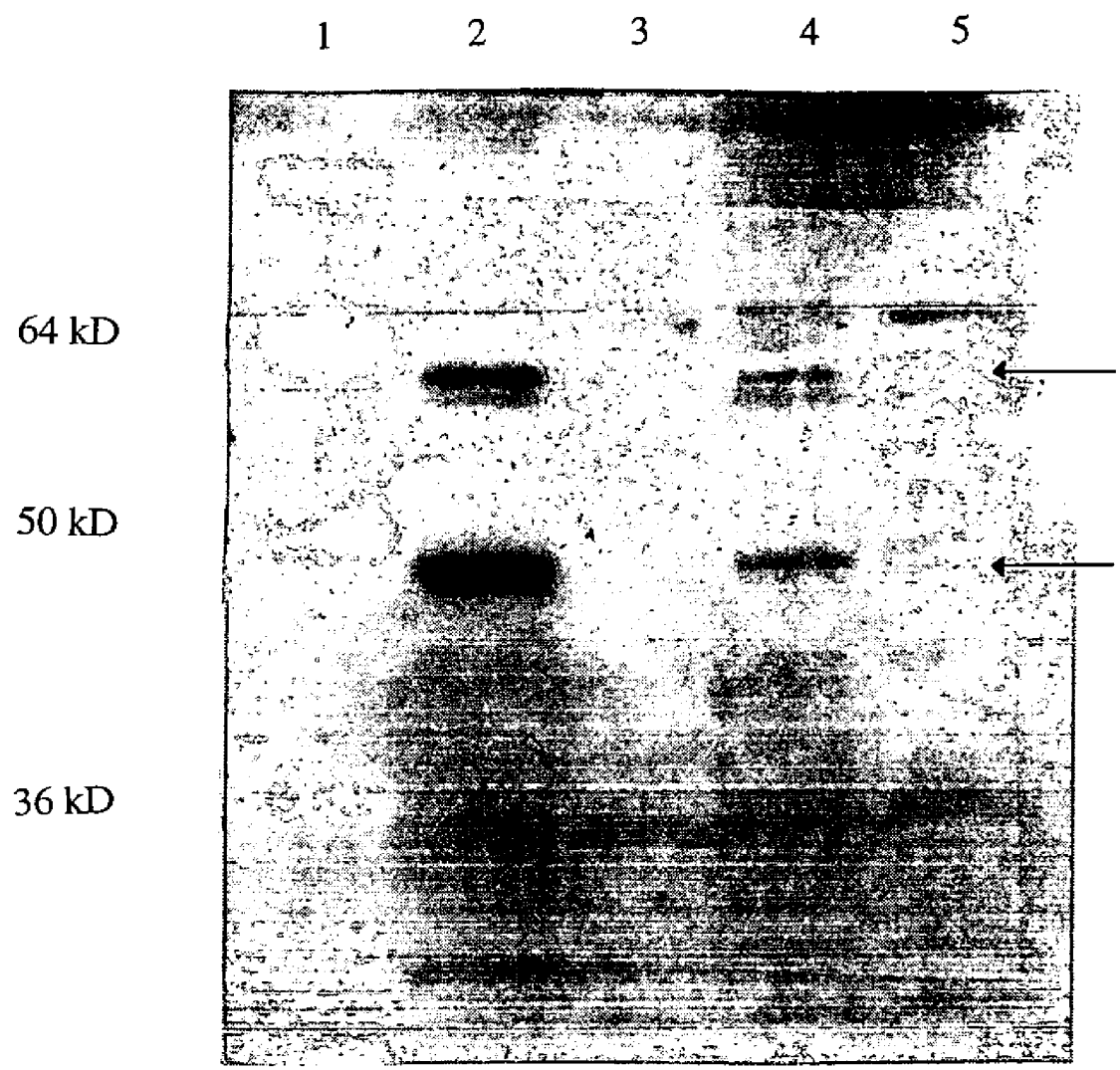
FIG. 6 shows western blot of SL3261-pHART. Lane 1 contains molecular weight standards. Lanes 2 and 4 contain whole cell lysates of SL3261-pHART. Lanes 3 and 5 contain whole cell lysates of control SL3261. Unique bands in lanes 2 and 4 are indicated with arrows.
Figure 7:
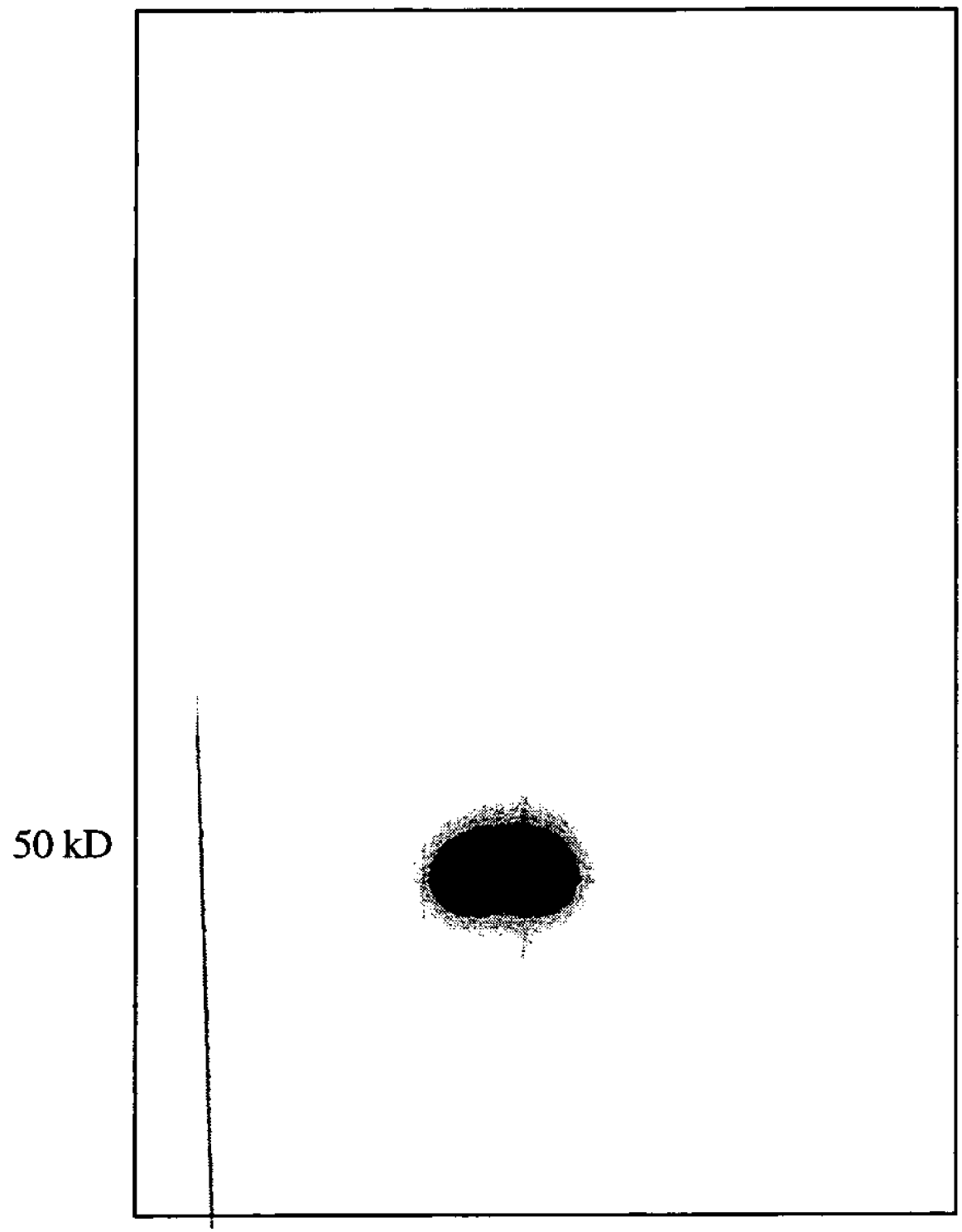
FIG. 7 shows western blot of inner and outer membrane isolation of SL3261-pHART. Lanes 1 and 2 contain the outer membrane fraction of SL3261-pHART and of control SL3261, respectively. Lanes 3 and 4 contain the inner membrane fraction of SL3261-pHART and of control SL3261, respectively.
Figure 8:
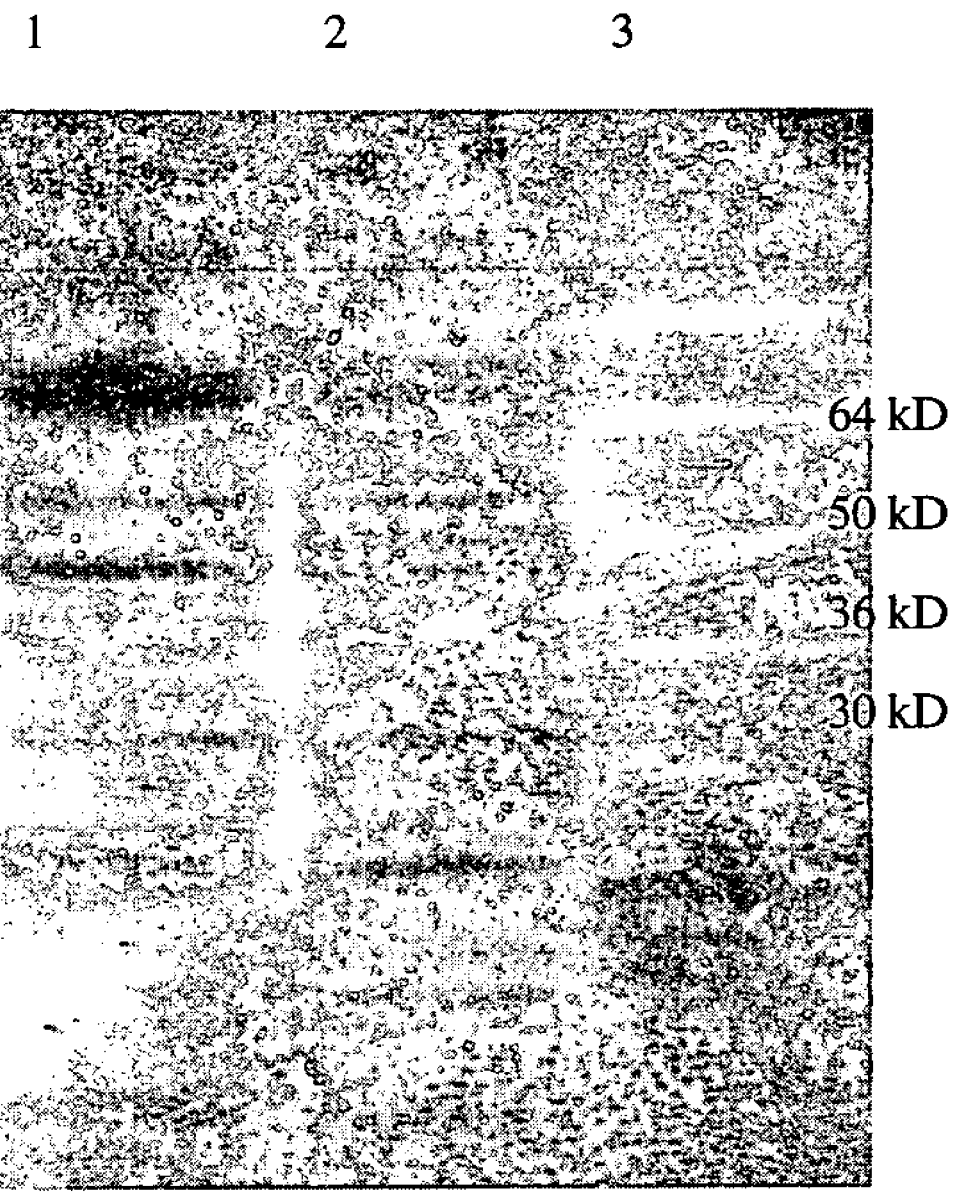
FIG. 8 shows western blot of SL3261-pHAT. Lane 1 and lane 2 contain the whole cell lysate of control SL3261 and of SL3261-pHAT, respectively. Lane 3 contains molecular weight standards. The unique band in lane 2 is indicated with an arrow.
Figure 9:
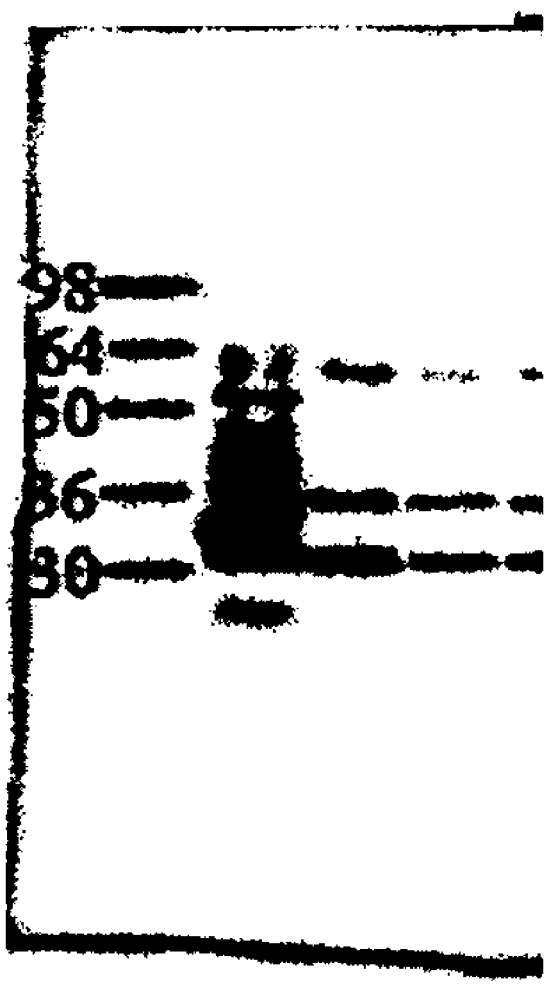
FIG. 9 shows western blot of inner and outer membranes from SL3261-pHAT and SL3261. Lane 1 contains molecular weight standards. Lanes 2 and lane 3 contain the outer membrane fraction of SL3261-pHAT and of control SL3261, respectively. Lane 4 and lane 5 contain the inner membrane fraction of SL3261-pHAT and of control SL3261, respectively.
Figure 10:
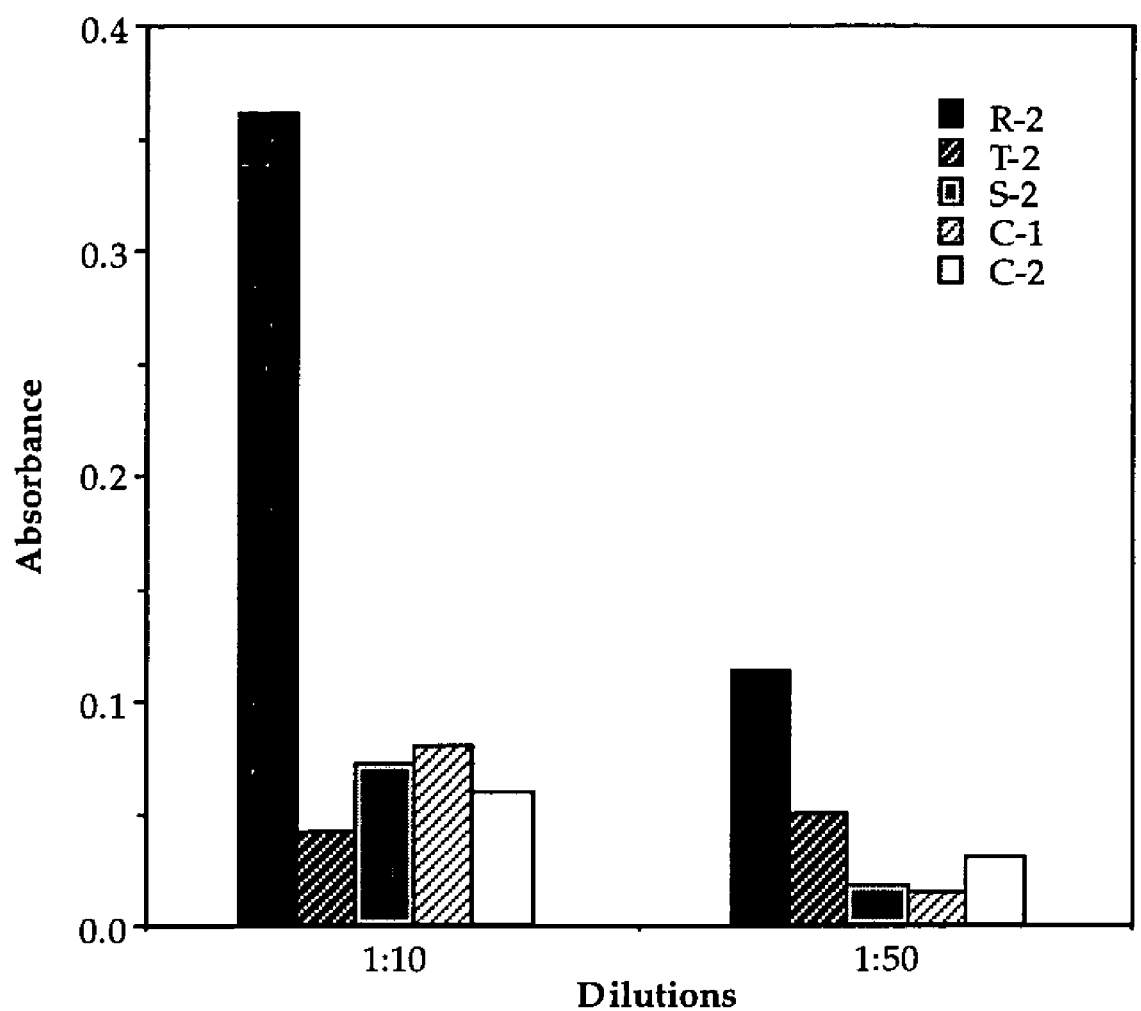
FIG. 10 shows graph of reverse transcriptase specific IgA measured in SL3261-pHART vaccinated mice at 9 weeks. Bar R-2, T-2, S-2, C-1 and C-2 represent the samples taken from SL3261-pHART vaccinated mice, SL3261-pHAT vaccinated mice, SL3261 vaccinated mice, control mice vaccinated with PBS and control mice vaccinated with PBS, kept on ampicillin, respectively.
Figure 11:
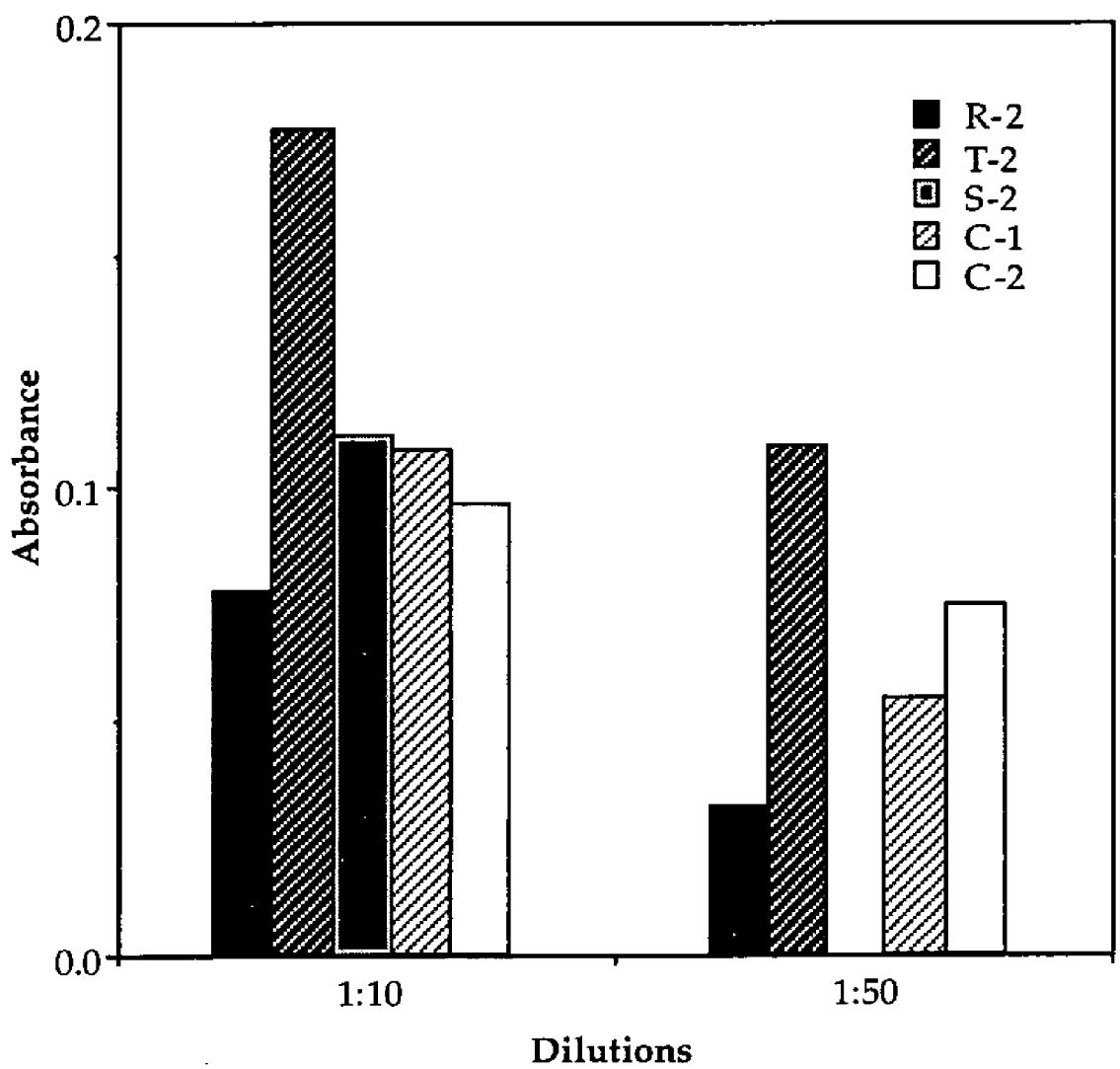
FIG. 11 shows graph of Tat specific IgA measured in SL3261-pHAT vaccinated mice at 9 weeks. Bar R-2, T-2, S-2, C-1 and C-2 represent the samples taken from SL3261-pHAT vaccinated mice, SL3261-pHAT vaccinated mice, SL3261 vaccinated mice, control mice vaccinated with PBS and control mice vaccinated with PBS, kept on ampicillin, respectively.
Figure 12:
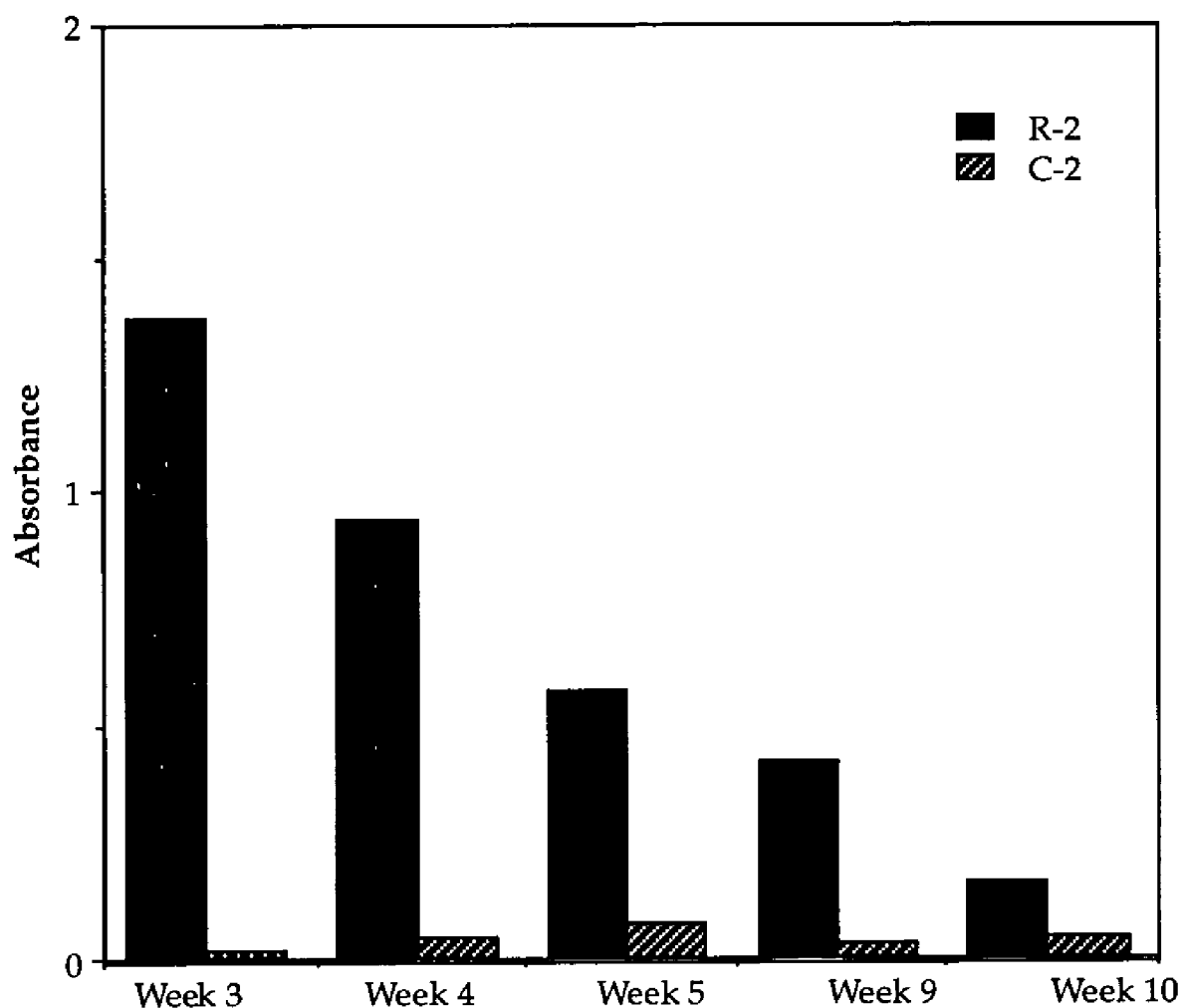
FIG. 12 shows a graph of reverse transcriptase specific IgA measured in SL3261-pHART mice over 10 weeks. The R-2 bars represent the samples taken from SL3261-pHART vaccinated mice who were kept on ampicillin. The C-2 bars represent the samples taken from control mice, fed PBS, and kept on ampicillin.
Figure 13:
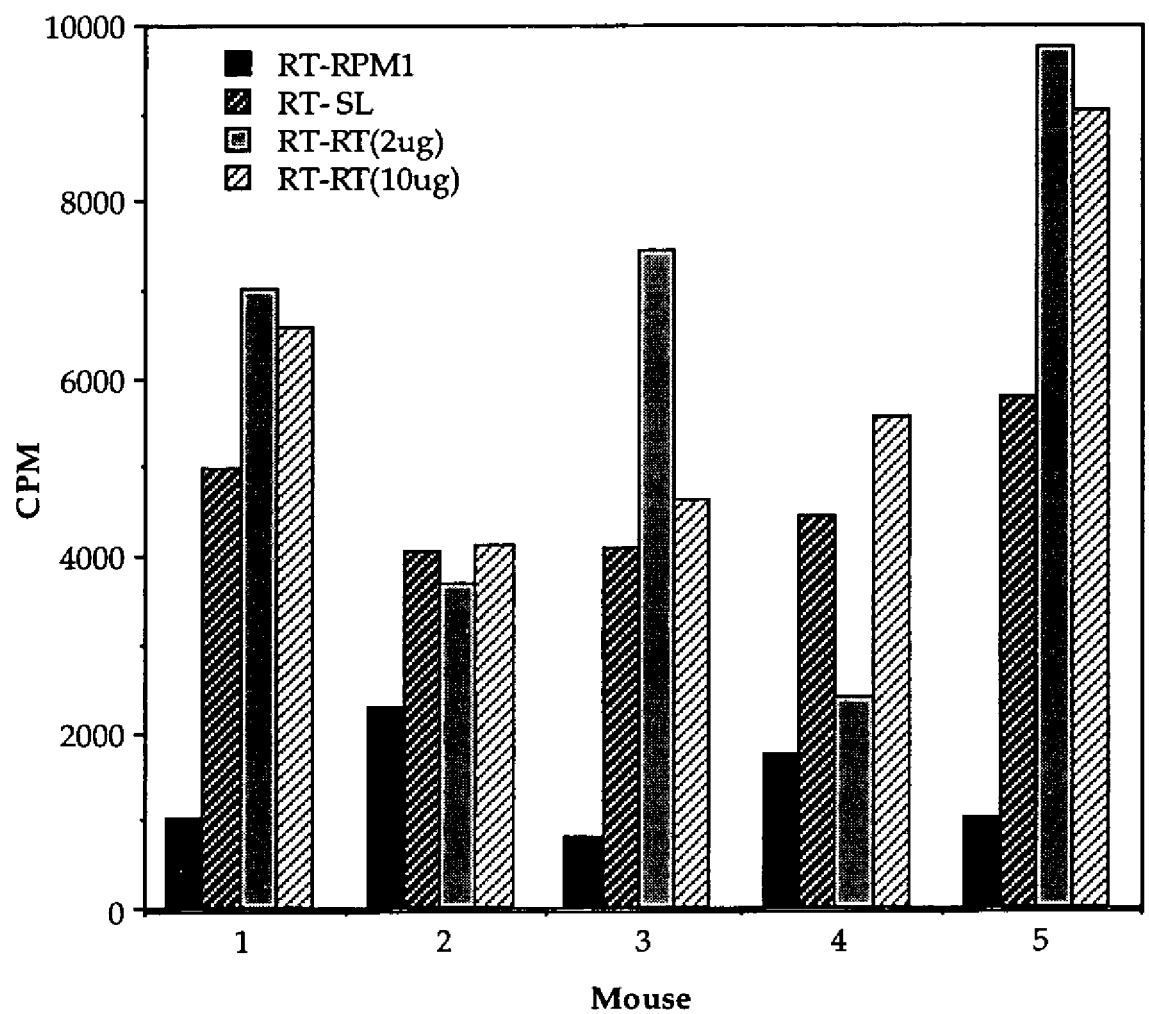
FIG. 13 shows proliferation response seen at 3 weeks in mice vaccinated with SL3261-pHART. The mice were all vaccinated with SL3261-pHART. Isolated splenocytes were incubated with either RPMI-1640 (control medium) as shown in the first bar (RT-RPMI), heat killed SL3261 (RT-SL bar), 2 μg of reverse transcriptase (RT—RT 2 μg bar) or 10 μg of reverse transcriptase (RT—RT 10 μg bar).
Figure 14:
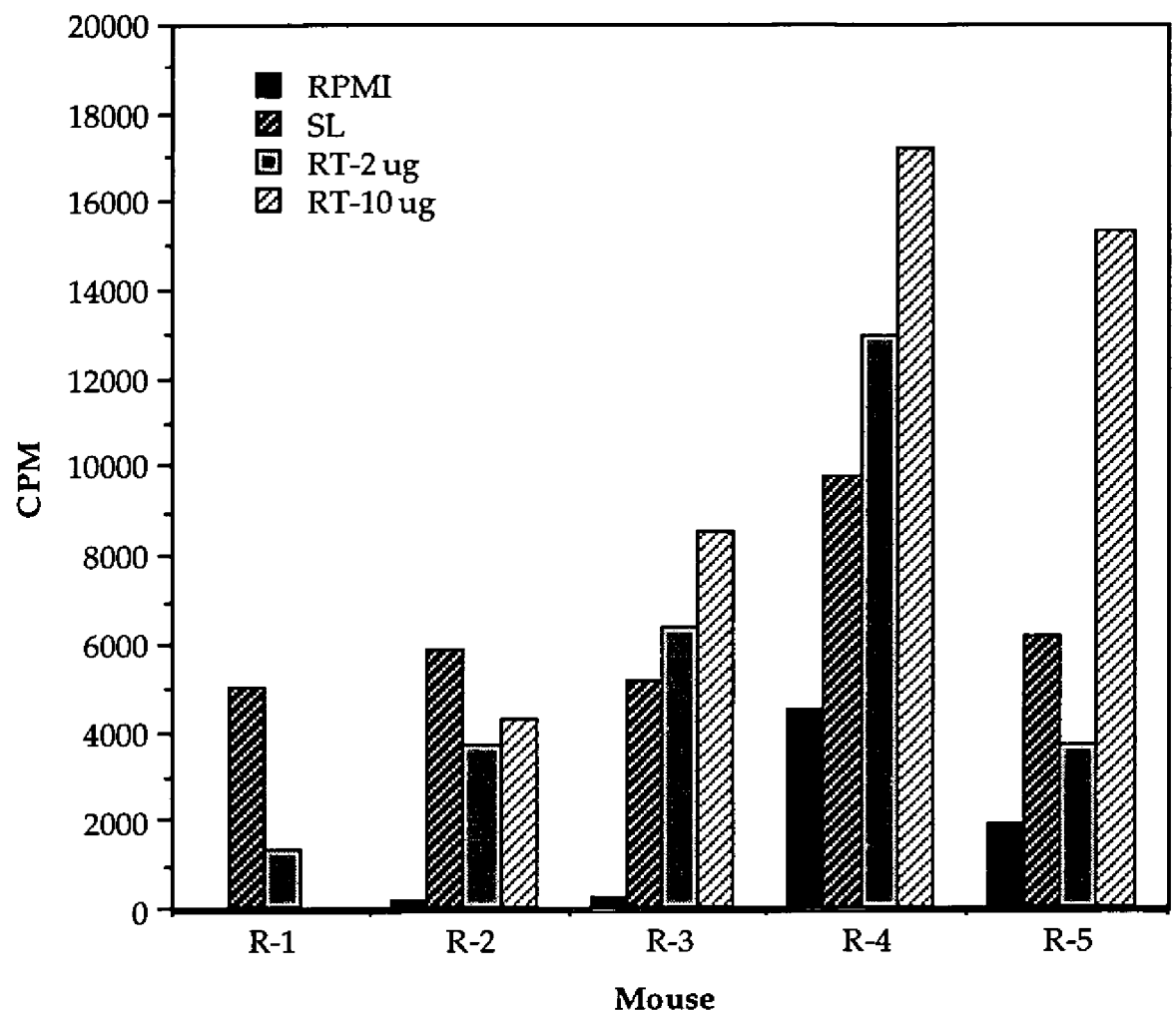
FIG. 14 shows proliferation results seen at 12 weeks in mice vaccinated with SL3261-pHART. The mice were all vaccinated with SL3261-pHART. Isolated splenocytes were incubated with either RPMI-1640 (control medium) as shown in the first bar (RPMI), heat killed SL3261 (SL bar), 2 μg of reverse transcriptase (RT 2 μg bar) or 10 μg of reverse transcriptase (RT 10 μg bar).

In the present invention, attenuated *Salmonella* SL3261 are used as a vehicle for delivering HIV antigens to the immune system by the method of surface expression; such live vaccines are used to orally inoculate mice and said animals are then tested for immune responses specific for the HIV antigens.

In one embodiment of the present invention, there is provided a fusion construct consisting of an *E. coli* lipoprotein (lpp) signal sequence linked to a portion of the *E. coli* outer membrane protein ompA. The lipoprotein signal sequence is necessary to direct the protein construct to the outer membrane of the gram negative bacteria, and consists of the first 9 amino acids of the N terminus. While this signal is needed for targeting to the surface, it is not itself surface exposed. For this reason, amino acids 46–159 of the ompA are added to the construct, as these residues code for five of the eight transmembrane regions that are present in the native OmpA protein. These five loops have a surface exposed C terminal end, which in this case, is fused to the heterologous protein. In early experiments, the periplasmic protein selected for surface exposure, was β-lactamase. Through methods such as immunofluorescence, cell fractionation and enzymatic activity assays, results indicated that the β-lactamase was indeed exposed on the outer surface of the *E. coli* (Francisco, Earhart, Georgiou, 1992).

In another embodiment of the present invention, there is provided HIV-1 reverse transcriptase protein as a HIV antigen. This protein was shown to be a target for cytotoxic T lymphocytes in infected humans (Walker, 1988, Lieberman, 1992, Rowland-Jones, 1995). Since a strong cell-mediated response is desired, this makes reverse transcriptase a good candidate. Additionally, the HIV-1 pol gene, which encodes the reverse transcriptase protein, has been found to be more highly conserved than other HIV-1 genes among different primary isolates (Hahn, et al., 1985). Other studies have determined that pol specific humoral cross-reactivity exists between HIV-1 and HIV-2, as well as considerable sequence homology (Clavel, 1986) (Guyader, 1987). Additionally, recent work has focused on using internal viral proteins as antigens, as opposed to envelope proteins, in the hopes of inducing a cell-mediated response.

In yet another embodiment of the present invention, there is provided HIV transactivating protein (Tat) as the second HIV antigen selected for surface expression. Li et al. (1995) found that HIV-1 Tat secreted from infected cells could induce cell death by apoptosis in T cells. Originally it was assumed that only cells infected with the HIV virus were destroyed, but later results obtained by Li (1995) uncovered the surprising fact that the number of infected cells is much smaller than the number of T cells that are actually lost. Something other than direct infection is responsible for the preponderance of T cell deaths, and one very likely candidate is the secreted HIV Tat protein. One additional hope in choosing the tat protein, was that any antibodies elicited by such a vaccine may provide protection for uninfected T cells, by neutralizing the secreted Tat. Another positive factor that led to the selection of Tat as an antigen was the identification of helper T cell epitopes (Blazevic, 1993).

In still another embodiment of the present invention, there is provided a model system for HIV vaccine construction. Using the genetic sequence for the lipoprotein-OmpA fusion, the genes for HIV-1 reverse transcriptase and HIV-1 tat are inserted so as to be surface expressed. These constructs are under the control of the lipoprotein promoter system, which is a leaky promoter that does not require induction. This is an important factor, as the bacterial vectors are administered to mammals, and induction of protein expression will not be an option.

In still another embodiment of the present invention, there is provided the attenuated strain of *Salmonella typhimurium*, SL 3261, wherein recombinant plasmids are electroporated. Expression experiments were repeated, and further studies were carried out to determine the location of the expressed HIV proteins. Specifically, bacterial inner and outer membranes were separated using sucrose gradients, and western blots of fractions were performed.

In still yet another embodiment of the present invention, there is provided BALB/c mice, wherein the live vaccine, consisting of SL3261 containing said recombinant plasmids, is administered orally. Mice were fed orally either the reverse transcriptase or tat live vaccine, SL3261 with no recombinant plasmid, or PBS. Vaccination was carried out on days 0, 14, and 28.

In still yet another embodiment, there are provided a series of vaccination assays in BALB/c mice, wherein weekly fecal samples were collected throughout the study, and assayed for IgA specific for reverse transcriptase or tat. At days 21 and 85, animals were sacrificed and splenocytes were isolated. Lymphocytes were assayed for helper T cell activity, by measuring either proliferative responses, or cytokine levels.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation Stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media. If the protein is secreted, this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than eight. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The labels most commonly employed for these studies are radioactive elements, enzymes, chemicals which fluoresce when exposed to ultraviolet light, and others. A number of fluorescent materials are known and can be utilized as labels. These include, for example, florescein, rhodamine, auramine, Texas Red, AMCA blue and Lucifer Yellow. A particular detecting material is anti-rabbit antibody prepared in goats and conjugated with fluorescein through an isothiocyanate.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

The present invention is directed to a live vaccine for human immunodeficiency virus (HIV) comprising a recombinant plasmid containing a gene required for surface exposure and a gene encoding a human immunodeficiency virus protein. Representative examples of a gene required for surface exposure is a gene which encodes E. coli lipoprotein signal sequence linked to a portion of the E. coli outer membrane protein ompA. A representative example of a gene encoding a human immunodeficiency virus protein is selected from the group consisting of reverse transcriptase and transactivating protein.

Preferably, the recombinant plasmid is electroporated into an attenuated bacterial host. A representative example of an attenuated bacterial host is a strain of Salmonella typhimurium, SL3261.

The present invention is directed to a method of producing an immune response specific for human immunodeficiency virus antigens in an individual in need of such treatment comprising the step of administering said individual with the claimed vaccine. Generally, a desired immune response comprises a mucosal IgA response, a helper T cell response and a cytotoxic T lymphocyte response.

The vaccine of the present invention is preferably administered orally. Preferably, the vaccine is administered in an oral dose of from about $10^{12}$ to about $10^{14}$ CFU (colony forming units).

The following examples are given for the purpose of illustrating various embodiments of the invention and are not meant to limit the present invention in any fashion:

EXAMPLE 1

Cloning of a Reverse Transcriptase-Lpp-OmpA Construct

The plasmid pKRT2 containing reverse transcriptase gene was obtained from the NIH AIDS Reagent Bank. A second plasmid, pTX101, containing the genes for the fusion protein construct of lpp-ompA was obtained from Dr. C. Earhart, at the University of Texas at Austin. A third plasmid, pSP72, was obtained from Promega. First, an intermediate plasmid pSP72-RT was constructed wherein the reverse transcriptase gene from the pKRT2 plasmid was transferred into the pSP72 plasmid. The reverse transcriptase gene contained in pKRT2 was modified by the polymerase chain reaction (PCR), to contain new restriction sites that would allow for insertion of the reverse transcriptase gene into the plasmid pSP72. Plasmids were digested with BamHI and HindIII, and run on 1% agarose gel to screen for the right clones.

The second step in the cloning involved inserting the lipoprotein promoter and lipoprotein-ompA sequence in front of the reverse transcriptase gene. The lipoprotein promoter and lipoprotein ompA fusion sequence was originally in the pTX101 plasmid. To insert lipoprotein-ompA sequence into pSP72-RT plasmid, complementary restriction sites are required. The HindIII site on the pSP72-RT plasmid was selected as the insertion site for the lipoprotein-ompA sequence. PCR primers were ordered from GIBCO LifeTechnologies to amplify the lipoprotein-ompA sequence with HindIII sites on either end using the pCRII-lipoprotein-ompA plasmid as a template. The reaction was set up containing 1 μl of template DNA diluted 1:10, 1 μl of each primer, and 45 μl of PCR supermix (GIBCO LifeTechnologies).

The PCR product and the purified plasmid pSP72-RT were digested with HindIII (LifeTechnologies) in a 20 μl reaction containing 2 μl of HindIII and 2 μl of REact 2 buffer (LifeTechnologies) for overnight at 37° C. The PCR product was purified following digestion by gel purification, ethanol precipitated, and then resuspended in 5 μl of water.

Following the digestion, the vector was dephosphorylated to ensure that vector could only ligate with insert, and not just religate with itself. To do so, the vector was ethanol precipitated and resuspended in 17 μl of water, 2 μl of 10× buffer, and 1 μl of shrimp alkaline phosphatase (United States Biochemical). The reaction was left for 1 hour at 37° C. The temperature was then increased to 65° C. for 15 minutes to inactive the phosphatase. The vector was then phenol/chloroform extracted, ethanol precipitated, and a portion was run on a gel to determine the concentration.

A ligation reaction was set up using 0.1 pmol of vector and 0.5 pmol of insert. The reaction volume was 10 μl, and contained 2 μl of T4 ligase buffer (33 μl 1M Tris-Cl pH 8, 5 μl 1M $MgCl_2$, 5 μl 1 M DTT, 5 μl 0.1M ATP, 1.25 μl 20 mg/ml BSA (bovine serum albumin), water to 100 μl), 1 ml of T4 ligase, and the vector and insert. The reaction was left at 16° C. overnight. The following day, the ligation mixture was diluted 1:5, and used to electroporate DH5α cells. Following electroporation, the cells were plated on LB amp plates and incubated overnight. Colonies were screened by cracking, and plasmids that ran higher than the control on a 1% agarose gel were selected for further screening. These cultures were grown up overnight, and the plasmids were purified using QIAgen prep kits. The purified plasmids were digested with HindIII to determine if the lipoprotein-ompA had been inserted. Since just one restriction site was used, the gene could be inserted backwards or forwards. To determine which plasmids contained the gene in the correct forward orientation, additional digestion was done, with XbaI and XhoI. If the lipoprotein-ompA fragment was inserted correctly, then a fragment of 300 bp would result. If the fragment were inserted backwards, the resulting fragment would be 450 bp in size. After identifying the correctly oriented plasmids, cultures were grown and frozen at −80° C. with glycerol. The resulting plasmid was called pHART.

Purified plasmid was sent to the sequencing facility at the University of Texas, at Austin for verification. To set up the sequencing reaction, 2 μl of primer, 1 μl of DNA, and 9 μl of water were combined in a 1.5 ml tube. The primers that were used were T7 and SP6 (Promega), as these sequences are found on the pSP72 plasmid.

EXAMPLE 2

Cloning of a Transactivating (Tat) Protein-Lpp-OmpA Construct

To construct a vector containing the genetic sequence resulting in the fusion protein of lpp-ompA-HIV-1 Tat, the gene for the Tat protein was obtained from the NIH AIDS Reagent Bank, supplied as a glycerol stock of DH5α, containing the plasmid pTAT. The plasmid pTAT contained the 288 bp tat sequence, engineered to contain codons preferred by E. coli. The tat gene was flanked by a HindIII site 5' to the gene, and followed by an EcoRI site. The plasmid that was selected to be the backbone, pSP72, contained both of these restriction sites in a multiple cloning region, so no alterations by PCR were needed. The first step was to insert the tat gene into the vector to construct an intermediate plasmid pSP72-Tat.

A culture was grown overnight of the *E. coli* containing the pTAT plasmid, and a second culture was grown of the *E. coli* containing the pSP72 plasmid, both in LB medium containing 100 µg/ml ampicillin. The desired plasmids were purified from these cultures using the Promega Wizard Prep kit. Plasmid DNA was then digested with HindIII and EcoRI restriction endonucleases (Promega), in the following reaction: 20 µl of DNA, 20 µl of water, 5 µl of 10× Multi-core buffer (Promega), and 2.5 µl of each enzyme. The reaction was incubated at 37° C. for 2 hours. The digests were then run on a 1% agarose gel. The 300 bp tat band from the pTAT digest was excised from the gel with a razor blade, as was the 2.4 Kb band corresponding to the digested pSP72 vector. Both were purified from the agarose using the Prep-A-Gene kit from BioRad. The gel purified DNA was then ethanol precipitated to remove any additional salts, resuspended in 10 µl of water, and used in a ligation reaction. The ligation reaction was set up as follows: 3 µl of digested pSP72, 4 µl of digested pTAT gene, 1 µl of 0.1 M ATP, 4 µl of 5× ligation buffer (LifeTechnologies), 1 µl T4 DNA ligase (LifeTechnologies), and 7 µl of water. The ligation was incubated overnight at room temperature (25° C.). The ligation reaction was then ethanol precipitated and resuspended in 10 µl of water. This concentrated DNA was used to electroporate *E. coli* DH5α cells. The electroporated cells were plated on LB agar plates containing 100 µg/ml ampicillin. Five colonies from the plate were screened to determine if they contained the correct insert. These colonies were grown up overnight in 5 ml cultures, and plasmid DNA was isolated using Wizard Prep kits. The DNA was then digested with Hind III and EcoRI. Several of the colonies showed an insert of 300 bp when the digests were run on a 1% agarose gel. This new recombinant plasmid was called pSP72-Tat. A glycerol stock was made of one of these cultures containing the proper insert, and stored at −80° C.

In order to complete the second step in the construct and add the lipoprotein promoter and lipoprotein-ompA sequence in front of the transactivating protein (tat) gene, the same approach for the reverse transcriptase construct was used. Purified plasmid pHAT was then sent to the sequencing facility at the University of Texas, at Austin for verification.

EXAMPLE 3

Expression of Reverse Transcriptase Construct in *E. coli*

A 3 ml overnight culture of control DH5α, and DH5α-pHART were grown in LB medium at 37° C. with shaking. The control cells were grown in plain LB medium, while the reverse transcriptase containing cells were grown in LB medium containing 500 mg/ml of ampicillin. The following day, 10 ml of LB amp, or LB were inoculated with 200 ml of these overnight cultures and grown for 4 hours. At this time, 5 ml of the DH5α-pHART culture was removed and placed in a fresh tube containing 50 ml of 0.1 M IPTG (isopropyl β-D-thiogalactopyranoside). The cells were grown for an additional 2.5 hours. 1 ml aliquots of control, DH5α-pHART induced and DH5α-pHART uninduced cultures were removed and pelleted in the presence of 40 ml of Complete Protease Inhibitors (Boehringer Mannheim). Cell pellets were resuspended in 60 ml water, 40 ml protease inhibitors, and 100 ml of 2× SDS Tris-Glycine sample buffer (Novex) containing DTT.

Samples were boiled for 5 minutes, then frozen at −80° C. Samples were thawed and boiled again for 5 minutes, then loaded onto a Novex 10% Tris-Glycine SDS gel. The voltage was set at 125 volts, and the gel was run for 2 hours. The samples were loaded onto the gel so that both halves were symmetrical. When gel was finished running, it was cut in half, and both halves were transferred to PVDF membranes for 1 hour at 56 mAmps. Following the transfer, the membranes were dried and left overnight.

The following day, membranes were dipped in methanol to wet, then stained with amido black to verify protein transfer. A photocopy was made of the stained PVDF membranes. The membranes were then destained and blocked with 3% BSA (bovine serum albumin) in PBS for 1 hour on shaker. Following the blocking, the membranes were ready for blotting with primary antibody. Membrane 1 was incubated with a cocktail of 4 monoclonal anti-reverse transcriptase antibodies at a dilution of 1:2000 for each antibody. Membrane 2 was incubated with a 1:5000 dilution of affinity purified polyclonal anti-reverse transcriptase antibodies purified. Both monoclonal and polyclonal antibodies were diluted in 10 ml of wash buffer (3% BSA (bovine serum albumin) in PBS with 0.05% Tween-20). After a 1 hour incubation with the primary antibody, the membranes were washed 6 times for 5 minutes each with wash buffer. Secondary antibodies were diluted 1:20,000 in 10 ml wash buffer. Goat a mouse antibody labeled with HRP was used for membrane 1, with the monoclonal primary antibodies, and goat anti-rabbit antibody labeled with HRP was used for membrane 2, with the polyclonal antibodies. Membranes were incubated with secondary antibody for 1 hour. Following this incubation, the membranes were washed 5 times for 10 minutes each with Sarkosyl buffer (50 mM Tris-Cl, pH 7.5, 1 M NaCl, 5 mM EDTA, 0.4% sarkosyl). The membranes were then rinsed well with water, and left in about 10 ml of water while carried to the darkroom. It is very important to keep the membranes wet. The SuperSignal (Pierce) was prepared by mixing 5 ml of luminol/enhancer solution with 5 ml of stable peroxide solution. Once in the darkroom, the water was removed from the membranes and the SuperSignal mix was added and allowed to incubate for 3–5 minutes. The membranes were then removed from the solution and placed on a piece of plastic wrap that was then folded over to cover the membrane. A piece of Hyperfilm-MP (Amersham) was cut to fit, and the membrane was exposed to the film for 15–30 seconds. Following the exposure the film was immediately developed.

Once the reverse transcriptase protein was found to be expressed in the *E. coli*, experiments were done to determine if the fusion construct was localized in the outer membrane. A crude membrane preparation was performed, to separate the outer membrane fraction from the total membrane fraction. These different fractions were then assayed by western blot to determine where the reverse transcriptase fusion construct was located. The western blots were performed as previously described.

EXAMPLE 4

Expression of Transactivating Protein (Tat) Construct in *E. coli*

The expression experiments and western blots for the Tat construct followed a very similar protocol as that for the reverse transcriptase cells. One difference is that b-mercaptoethanol was added to the 2× Novex Tricine Sample buffer, instead of using DTT as the reducing agent. The samples were also run on a 10–20% Tricine gel. The primary antibody used was a polyclonal anti-tat antibody that was obtained from the NIH AIDS Reagent bank, and used at a 1:1000 dilution.

EXAMPLE 5

Expression of Reverse Transcriptase Construct in *Salmonella* SL3261

Purified pHART plasmid was electroporated into electrocompetent *Salmonella* SL3261. Plasmid uptake was verified using restriction digests. All experiments in SL3261 were done with uninduced cells.

In order to load the more viscous *Salmonella* samples onto a gel, the DNA first had to be sheared by pipetting up and down through first a 20 gauge needle, then a 26 gauge needle. Samples were then centrifuged for 10 minutes at 10,000 rpm in a microcentrifuge. Reverse transcriptase samples were loaded onto a Novex 10% Tris-Glycine gel, and protein bands were separated. The best western blots were obtained for reverse transcriptase when no reducing agent was added to the samples prior to loading on the gel. One additional procedure that was employed to further characterize the SL3261 samples was a separation of inner and outer membranes using a sucrose gradient. This method of separating membrane fractions is cleaner than the crude membrane preparation that was used for the *E. coli* samples. Once inner and outer membrane fractions were obtained for both control SL3261 and SL3261 containing the pHART plasmid, these samples were run on an SDS gel, and assayed by western blot, using anti-reverse transcriptase antibodies, as previously described.

EXAMPLE 6

Expression of Transactivating Protein (tat) Construct in *Salmonella* SL3261

Purified pHAT plasmid was electroporated into electrocompetent *Salmonella* SL3261, and plasmid uptake was verified by appropriate restriction digestion. As with the reverse transcriptase construct samples, induction experiments were not performed.

Samples were prepared for gel loading in the same manner as described above, and then loaded on a Novex 10–20% Tricine gel. A unique band was visible on a western blot in the lanes containing the Tat sample when β-mercaptoethanol was added as a reducing agent. If samples were not reduced prior to loading on the gel, the band would disappear in the Tat western blots.

As with the reverse transcriptase samples, an inner and outer membrane isolation using a sucrose gradient was performed. These samples were likewise assayed by western blot, using both anti-Tat antibodies and anti-ompA antibodies. Due to the high levels of non-specific binding seen with the anti-Tat antibodies, the western blots were very inconclusive. More positive results were obtained when using anti-ompA antibodies in the western blot.

EXAMPLE 7

Vaccination for IgA and Proliferation Assays

In order to test the efficacy of the vaccine, mice were fed doses of attenuated *Salmonella* SL3261 containing the HIV fusion constructs. Mucosal and helper T cell immune responses were monitored. The mucosal response was monitored by collecting fecal samples and assaying for anti-reverse transcriptase IgA, and the helper T cell response was measured by proliferation assays and cytokine assays. The proliferation assays involved incubating splenocytes with antigen and then spiking with $^3$H-thymidine. Cells that are proliferating and therefore responding to the antigen will take up more radioactive thymidine than cells that are not responding. Once cells are harvested and counted, the higher counts indicate more proliferation and therefore antigen recognition. The cytokine assays involved removing supernatant from cells that were incubated with antigen. Cells that are stimulated by antigen will secrete different cytokines into the supernatant. The levels of IL-2 and IL-10 can be measured using sandwich ELISAs. High IL-2 levels indicate a helper T cell response ($T_{H2}$ response), while higher IL-10 levels indicate a cytotoxic T cell response ($T_{H1}$ response).

Bacterial cultures were grown in 50 ml of LB medium with or without 500 µg/ml ampicillin as appropriate. Cultures were shaken for 22 hours at 37° C. Cells were pelleted at 5,000 rpm for 10 minutes, then resuspended in 500 µl of PBS. 30 µl aliquots were placed in labeled 0.5 ml tubes and kept on ice until feeding.

5 week old BALB/C mice were obtained from Jackson Labs. Mice were divided into 4 groups of 10 and housed 5 per cage. Mice were aged 2 weeks prior to start of the experiment. Mice were vaccinated as follows: Food and water was removed 4 hours prior to vaccinations. Prior to bacterial dose, mice were fed 10 µl of 6% sodium bicarbonate with a pipette tip. After waiting 10 minutes, mice were fed the appropriate bacteria. One group of mice, labeled R was fed 20 µl of SL3261-pHART. A second group labeled T, was fed 20 µl of SL3261-pHAT. A third group of mice, S, was fed 20 µl of control SL3261, and a fourth group, C, was fed 20 µl of PBS (Table 1). Mice in the R group, housed in cages R-1 and R-2, were kept on ampicillin throughout the study due to plasmid stability problems. Fresh water was provided daily, containing 1 g/L ampicillin. Mice in the C-2 cage were kept on the same dose of ampicillin to rule out any effects of the antibiotic on the immune response. Vaccine doses were given to all mice on days 0 and 14. On day 21, one cage of R, T, S, and two mice from each C cage, C-1 and C-2, were sacrificed for the 3 week study. The remaining mice were dosed again on day 28, and on day 85, mice were sacrificed for the 12 week study.

TABLE 1

Schedule of Mouse Vaccinations for IgA and Proliferation Studies

| | 10 R Mice | 10 T Mice | 10 S Mice | 10 C mice |
| --- | --- | --- | --- | --- |
| Day 0 | 20 µl SL3261-reverse transcriptase | 20 µl SL3261-Tat | 20 µl SL3261 | 20 µl PBS |
| Day 14 | 20 µl SL3261-reverse transcriptase | 20 µl SL3261-Tat | 20 µl SL3261 | 20 µl PBS |
| Day 21 | 5 Mice sacrificed | 5 Mice sacrificed | 5 Mice sacrificed | 4 Mice sacrificed |
| Day 28 | 20 µl SL3261-reverse transcriptase | 20 µl SL3261-Tat | 20 µl SL3261 | 20 µl PBS |
| Day 85 | 5 Mice sacrificed | | 5 Mice sacrificed | 4 Mice sacrificed |

EXAMPLE 8

Collection of Fecal Pellets for IgA Assays

To monitor mucosal IgA response, fresh droppings were collected weekly from each cage of mice and placed in a 2 ml microfuge tube. 1 ml of PBS was added to each tube and samples were left for 1–2 hours, with occasional vortexing. Samples were centrifuged at 14,000 rpm for 15 minutes. Supernatant was removed to a clean tube and stored at −80° C.

The IgA ELISAs were performed as follows: Nunc 96 well polystyrene plates were pre-coated overnight with 200 ng of reverse transcriptase or Tat in 50 µl of PBS. Plates were kept at 4° C., wrapped in plastic wrap and in a sealed plastic container with a moist paper towel. The next day, antigen was poured off, and plates were washed 3 times with wash buffer (0.05% Tween-20 in PBS). Plates were then blocked for 2 hours with 200 µl of 3% bovine serum albumin in PBS at room temperature. Following blocking step, plates were washed 3 times with wash buffer. Freshly diluted, re-centrifuged samples were added at 100 µl per well. Samples were diluted 1:10 and 1:50 in 3% bovine serum albumin in PBS. Plates were incubated at room temperature for 2.5 hours. Following samples binding, plates were washed 4 times with wash buffer. A 100 µl volume of Goat-anti Mouse IgA (Sigma, labeled with Horseradish Peroxidase) diluted 1:500 in 3% bovine serum albumin in PBS was added to each well. Plates were incubated 1 hour at room temperature. Plates were then washed 4 times with wash buffer, and 100 µl of ABTS (2,2'-Azinobis(3-ethylbenzthiazoline sulfonic acid)) was added to each well. After sufficient color development, reaction was stopped by adding 100 µl of oxalic acid. Plates were then read at 414 nm on a BioRad plate reader.

EXAMPLE 9

Proliferation Assays and Cytokine Assays

Mice were sacrificed by cervical dislocation in sterile conditions. Spleens were removed and placed in 60×15 mm petri dishes containing 3 ml of RPMI 1640 (LifeTechnologies) containing 2 mM L-glutamine, 50 µg/ml gentamicin, 50 µM β-mercaptoethanol, and 10% fetal calf serum (LifeTechnologies). Small intestines were removed and placed in a sterile 15 ml tube containing 5 ml 50 mM EDTA, 2 mg/ml soybean trypsin inhibitor (Sigma). Livers were removed and placed in a sterile 15 ml tube containing PBS. Livers and intestines were kept on ice until frozen at −80° C.

Spleens were cut into small pieces using a pair of scissors and forceps. Tissue was then pressed against the bottom of the dish using the flat top of a plunger from a 5 ml syringe. This was repeated until only fibrous tissue remained. The suspension was then drawn up and down through a 19 gauge needle several times then passed through a nylon mesh screen and placed in a sterile 15 ml tube on ice. The petri dish was rinsed with an additional 4 ml of RPMI-1640, which was then added to the 15 ml tube. From this point on, all splenocyte samples were kept on ice.

Splenocytes were then centrifuged at 1250 rpm for 10 minutes and supernatant was removed. The remaining red pellet was resuspended in 5 ml sterile lysing buffer (0.15 M $NH_4Cl$, 1.0 mM $KHCO_3$, 0.1 mM EDTA, pH 7.4) to lyse the erythrocytes. Splenocytes were incubated for 5 minutes at room temperature with occasional shaking. After the incubation period, RPMI medium was added to fill the tube to 13 ml, and samples were centrifuged at 1250 rpm for 10 minutes. Supernatant was discarded and cells were washed with media again. Following the second wash, the white pellet was resuspended in 5 ml RPMI, 10% fetal calf serum.

All samples were counted using a hemocytometer. 50 µl from each well-resuspended sample was added to 450 µl of trypan blue. A drop of this solution was placed on a hemocytometer, and live cells, which do not take up the blue dye, were counted.

Cells from the control mice were needed as the antigen presenting cells, and thus had to be treated with mitomycin C (Sigma) to inhibit proliferation. Before this procedure, a portion of each sample of control cells was removed and set aside to be used as control responder cells. The remaining control cells were centrifuged for 10 minutes at 1250 rpm. Supernatant was removed and cells were resuspended in 2 ml of sterile PBS/tube. Mitomycin C was prepared by resuspending 2 mg in 4 ml of PBS and filter sterilizing. The tube containing mitomycin was wrapped in aluminum foil to protect from the light at all times. 100 µl of mitomycin solution was added per ml of cells, or 200 µl per tube. Tubes were wrapped in aluminum foil, and incubated at 37° C. for 20 minutes. RPMI, 10% fetal calf serum was added to samples to fill the tubes to 13 ml. Cells were centrifuged at 1250 rpm for 10 minutes and supernatant was discarded. The wash was repeated two additional times. These inactivated effector cells were resuspended in a 5 ml volume of RPMI, 10% fetal calf serum and recounted using a hemocytometer as described above. All samples were adjusted to concentrations of $1 \times 10^6$ cells/ml by appropriate dilution in medium and left on ice until ready for plating.

For both the proliferation assays and the cytokine assays, plates were set up the in the same way. The antigens that were tested were either recombinant reverse transcriptase or Tat at concentrations of 10 µg/ml or 50 µg/ml, heat killed SL3261, or RPMI. To prepare the heat killed SL3261, culture was grown overnight in LB medium. Two ml of cells were removed and heated at 65° C. in a 2 ml microcentrifuge tube for 2 hours. The cells were then spun down and resuspended in 2 ml of sterile PBS. Cells were used in assays by preparing a 1:10 dilution in RPMI, 1 ml of SL3261 in 9 ml of RPMI.

Properly diluted antigen was added to each well in a 50 ml volume. Next, $1 \times 10^5$ effector cells (control cells treated with mitomycin C) were added to each well in a 100 µl volume. The responder cells to be tested were then added, $1 \times 10^5$ cells per well in a 100 µl volume. All samples were set up in triplicate. Plates were covered and incubated at 37° C. with 5% $CO_2$.

For the cytokine experiments, plates were incubated for 48 hours. At this time, 150 µl of supernatant was removed from each well. The 150 µl aliquot from each triplicate was combined in a 0.5 ml tube containing 10 µl of Complete™ Protease Inhibitors (Boehringer Mannheim, 1 tablet/1 ml water). Samples were stored at −80° C. until used in ELISAs.

For proliferation experiments, the plates were incubated for either 3 or 5 days. 18 hours prior to harvesting the cells, wells were spiked with 1 mCi of $^3$H-thymidine. The radioactive thymidine (1 µCi/µl) was diluted as follows: 200 µl of $^3$H-thymidine was added to 3800 µl of RPMI medium, resulting in a concentration of 50 µCi/ml. 20 µl of this dilution was added to each well, for a final concentration of 1 µCi/well. The plates were returned to the incubator at 37° C. and 5% $CO_2$ for 18 hours.

A Brandel M-24 cell harvester was used to collect the cells on Whatman glass filters. Filters were then placed in liquid scintillation vials with 5 ml of Econofluor liquid scintillation cocktail and samples were counted on a Beckman LS6000SC.

The interleukin ELISAs to determine concentrations of IL-2 and IL-10 were performed as described.

EXAMPLE 10

The present invention discloses development of a model live vaccine for HIV by surface expressing HIV antigens in an attenuated strain of *Salmonella* to produce a cellular and mucosal immune response as well as a humoral response. As described above, an intermediate plasmid, pSP72-RT or pSP72-Tat was first constructed, and then used as a backbone for the insertion of the Lpp-OmpA sequence, ultimately resulting in the desired recombinant plasmid pHART (FIG. 1) or pHAT (FIG. 2).

Once both plasmids were constructed and sequenced, the expression of the fusion proteins were assayed first in *E. coli* DH5α. FIG. 3 is an image of the western blot of *E. coli* DH5α-pHART. Unique bands are seen in the lanes containing samples from the pHART containing bacteria. The lane containing the control *E. coli* DH5α which does not have the recombinant plasmid does not show these bands on the western blot. The presence of these unique bands indicates that expression of the HIV reverse transcriptase protein is indeed occurring.

Similar results were obtained when samples of *E. coli* DH5α-pHAT were analyzed by a western blot stained with anti-Tat antibodies (FIG. 5). In this blot, bands that are unique to the *E. coli* containing pHAT can be seen, that do not appear in the control *E. coli* lane. The control *E. coli* do not contain the recombinant pHAT plasmid with the tat gene.

To further characterize the location of the HIV Reverse Transcriptase antigen, a crude membrane preparation was performed. Total membrane and outer membrane samples from control *E coli*, and pHART containing *E coli* were assayed using a western blot stained with anti-reverse transcriptase antibodies. The results of this western blot are shown in FIG. 4. The same unique bands that are present in the whole cell lysates of the *E. coli* DH5α are present in both the total membrane fraction and the outer membrane fraction. This result indicates that the HIV reverse transcriptase is localized in the outer membrane of these bacterial cells.

Once it had been established that both reverse transcriptase and tat could be detected in the DH5α*E. coli* cells, the recombinant plasmids pHART and pHAT were then transformed into the attenuated strain of *Salmonella* SL3261 and expression of the fusion proteins was verified. Polyclonal anti-reverse transcriptase antibodies were used to stain the western blot of SL3261-pHART, shown in FIG. 6. As with the *E. coli*, two unique bands were present in the *Salmonella* samples. The presence of these unique bands of the appropriate molecular weight indicates that expression of the reverse transcriptase protein is indeed occurring. Polyclonal anti-Tat antibodies were used to stain the western blot of SL3261-pHAT, shown in FIG. 8. A unique band is seen only in the lane containing the pHAT plasmid, but not in the control SL3261. This band runs higher than the expected molecular weight, which may be the result of solubilization problems with the ompA protein in SDS.

To better localize the HIV reverse transcriptase in the *Salmonella* system, inner and outer membranes were isolated and analyzed by a western blot, shown in FIG. 7. A single band only visible in the outer membrane fraction of cells containing pHART indicates that the reverse transcriptase protein is localized to the outer membrane of the attenuated *Salmonella*. A separation of inner and outer membranes of SL3261 containing pHAT was also done. The results of the western blot are shown in FIG. 9. Unique bands present in the outer membrane fraction of the SL3261 containing pHAT are of the same molecular weight as the unique bands seen in westerns of whole cell lysates of SL3261-pHAT, which suggests that the HIV Tat protein is localized to the outer membrane of these cells.

EXAMPLE 12

Once the constructed live vaccines, consisting of the attenuated strain of *Salmonella* SL3261 containing either the plasmid pHART or pHAT were determined to be expressing the appropriate HIV proteins, these bacteria were used to vaccinate mice. Following the oral administration of two to three doses, the mice were assayed for immune responses to the appropriate HIV antigen.

In the first series of experiments, mice were assayed for secretory IgA responses to HIV reverse transcriptase (FIG. 10) and to HIV tat (FIG. 11). A specific IgA response is only seen in the mice vaccinated with either SL3261-pHART or SL3261-pHAT, which indicates that both vaccines indeed induce some specific IgA response, although there is over a two-fold better response in the mice vaccinated with the reverse transcriptase vaccine to the reverse transcriptase antigen, than there is with the Tat vaccine against the Tat antigen.

FIG. 12 shows a graph of the reverse transcriptase specific IgA response obtained in the SL3261-pHART vaccinated mice over time. The response appears to decline over time, following a peak at 3 weeks after the first vaccination. This decrease in reverse transcriptase specific antibody could possibly be explained by a phenomenon often seen with live vaccine constructs. When the mice are first inoculated with the live vaccine, they raise antibodies not only against the desired antigen (in this case, the reverse transcriptase) but also against the *Salmonella*. Further doses to increase the immune response to the specific antigen may be less effective, due to the higher levels of anti-*Salmonella* antibodies present in the mucosa, which cause a decrease in the number of *Salmonella* that can successfully infect the mouse (Kraehenbuhl, 1992). These higher levels of anti-*Salmonella* antibodies essentially serve to lower the effective dose of the vaccination.

Proliferation assay was done to measure the helper T cell response specific for the HIV antigens. A short, 3 week study shows that despite high background, it appears to be a reverse transcriptase specific response developing in these SL3261-pHART vaccinated mice 3 weeks after the first vaccination (FIG. 13). Results from assays against the Tat antigen are less promising (data not shown).

FIG. 14 shows a 12 week study after initial vaccination with the reverse transcriptase vaccine as were done in the 3 week study. Here, the responses seen in the splenocytes isolated from the different mice is more pronounced. Four out of the five mice vaccinated with the SL3261 containing the reverse transcriptase construct show a positive response to the two concentrations of reverse transcriptase antigen used to stimulate the splenocytes. All of the five mice show a positive response to the heat-killed *Salmonella* used to stimulate the splenocytes. This positive response to the *Salmonella* is expected, as the mice were exposed not only to the reverse transcriptase antigen, but also to the *Salmonella* carrier. All five mice showed background levels of proliferation when the splenocytes were incubated with RPMI-1640 medium alone. These results were very positive indicating that when vaccinated with the live vaccine expressing the HIV reverse transcriptase antigen, these mice will develop a helper T cell response specific to the reverse transcriptase.

The present invention demonstrates the development of a live vaccine for HIV by surface expressing HIV antigens in an attenuated strain of *Salmonella* so as to produce a cellular and mucosal immune response as well as a humoral response. By using an attenuated strain of *Salmonella* for the live vaccine vector, one can elicit both a cellular and a mucosal response.

The first steps in developing the vaccine of the present invention involved constructing two plasmids for transformation into the attenuated strain of *Salmonella*. These plasmids both contained the lpp-ompA fusion construct under the control of the lpp promoter, which allows for constant expression of the protein construct. The lpp-ompA genes were followed by the gene for either the HIV reverse transcriptase protein or the HIV tat protein. This tripartite fusion construct resulted in expression of the HIV proteins on the outer surface of the bacteria.

Following the construction of these plasmids, whether the HIV proteins were expressed in the bacteria was determined. Methods for detecting expression in an *E. coli* strain were developed and the plasmids were transformed into the attenuated *Salmonella* strain. Protein expression was assessed and the proteins were localized. Following additional characterization of the live vaccine, mice were fed doses of the recombinant attenuated *Salmonella*, and their immune responses were monitored. Production of a mucosal immune response was assessed by measuring fecal IgA levels, helper T cell response was examined by performing proliferation assays and measuring cytokine levels.

In the construction of the recombinant plasmids, the first step was to construct two plasmids, one of which contains an lpp-ompA fusion sequence, followed by the HIV reverse transcriptase gene, under the control of the lpp promoter. The second plasmid contained the same lpp-ompA fusion sequence followed by the HIV tat protein. Each of these plasmids were constructed using the pSP72 plasmid as a backbone. This agarose gel of multiple restriction digests showed the desired fragments of the expected size. These recombinant plasmids contained the desired lpp-ompA gene fragments, as well as the appropriate HIV gene sequences.

Once the plasmids were constructed, whether the HIV proteins were expressed in a bacterial system was shown. Whole cell-lysates of *E. coli* containing the recombinant plasmid both induced with IPTG and uninduced, as well as control *E. coli* without the plasmids were run on an SDS gel, and transferred to PVDF membranes for western blotting. The HIV reverse transcriptase protein was detectable on a western blot. The membrane was stained with a polyclonal anti-reverse transcriptase antibody. There were two unique bands at the desired molecular weight that are only present in the *E. coli* containing the recombinant pHART plasmid. The antigen was purified from *E. coli*.

The sample containing the induced bacterial cells does not appear any different from the sample containing the uninduced bacterial cells. The bacteria containing the recombinant plasmids for surface expression were not as healthy as control bacteria, and the plasmid is not very stable. The growth rate of the recombinant SL3261 was slower than the growth rate of the control SL3261. The plasmid stability of pHART in SL3261 grown without antibiotics was 12%. Plasmid stability of pHAT in SL3261 was at 90%. These factors of slower growth rate and plasmid instability may decrease the amount of protein expression seen upon induction.

To further characterize the location of the HIV reverse transcriptase antigen, a crude membrane preparation was used to separate the outer membrane from the total membrane fraction. These membrane samples were analyzed by a western blot stained with anti-reverse transcriptase antibodies. In the western blot, the same unique bands that were present in the whole cell lysates of the DH5α *E. coli* were present in both the total membrane fraction and the outer membrane fraction. This result indicates that the HIV reverse transcriptase was localized in the outer membrane of these bacterial cells.

In a western blot of whole cell lysates containing the recombinant plasmid pHAT, with the HIV tat gene, induced, uninduced, and with control *E. coli*, stained with a polyclonal anti-tat antibody showed bands that were unique to the bacteria containing the recombinant plasmid. Some non-specific binding of antibody were also present in the anti-tat western blot. Likewise, the levels of protein expression do not appear to differ in the induced and uninduced bacteria.

As both reverse transcriptase and tat were detected in the DH5α *E. coli* cells, the recombinant plasmids pHART and pHAT were then transformed into the attenuated strain of *Salmonella* SL3261. A western blot was done of whole cell lysates using SL3261 containing the reverse transcriptase pHART plasmid. The antibody used for detection of expression was affinity purified polyclonal anti-reverse transcriptase. As with the *E. coli*, two unique bands are present in the *Salmonella* samples. The presence of these unique bands of the appropriate molecular weight indicates that expression of the reverse transcriptase protein occurred.

To better localize the HIV reverse transcriptase in the *Salmonella* system, inner and outer membranes were isolated using a sucrose gradient, and these samples were analyzed by a western blot. In a western blot, a single band was visible in the outer membrane fraction of cells containing the recombinant pHART plasmid. Thus, the reverse transcriptase protein was localized to the outer membrane of the attenuated *Salmonella*.

As with the recombinant reverse transcriptase plasmid, a western blot was done of the whole cell lysates of SL3261 containing the pHAT plasmid with the HIV tat gene. Polyclonal anti-tat antibodies were used to stain the western blot. A unique band was seen in the lane containing the pHAT plasmid and not in the control SL3261. This band was running around 50 kDa, which is higher than the expected molecular weight.

A separation of inner and outer membranes of SL3261 containing the plasmid pHAT was done to further localize the recombinant tat. A western blot was stained with anti-ompA antibodies and unique bands were present in the outer membrane fraction of the SL3261 containing the recombinant pHAT plasmid. These bands were running higher than expected for this fusion construct, with a molecular weight of around 50 kDa. A definite difference was observed between the pHAT containing SL3261 and the control SL3261. These unique bands are of the same molecular weight as the unique band seen in the westerns of whole cell lysates of SL3261-pHAT stained with anti-tat antibodies and suggest that the HIV tat protein is localized to the outer membrane of these cells. The HIV antigens reverse transcriptase and tat were expressed in these tripartite fusion constructs in *E. coli* and attenuated *Salmonella*. Both the reverse transcriptase and tat proteins were localized to the bacterial outer membrane.

Once the constructed live vaccines, consisting of the attenuated strain of *Salmonella* SL3261 containing either the plasmid pHART or pHAT were determined to be expressing the appropriate HIV proteins, these bacteria were used to vaccinate mice. Following the oral administration of two to three doses, the mice were assayed for immune responses to the appropriate HIV antigen. The method of oral vaccination was chosen for this study. Mice were assayed for secretory IgA responses to HIV reverse transcriptase and HIV tat over a period of 12 weeks. These same mice were also assayed for a helper T cell response by performing proliferation assays on isolated splenocytes.

A difference in IgA levels was seen in the reverse transcriptase specific IgA measured in the vaccinated mice. Only the mice vaccinated with SL3261-pHART had such high levels of reverse transcriptase specific IgA. In the mice vaccinated with the SL3261-pHAT live vaccine levels of tat specific IgA, a specific response was seen. These results were positive and indicate that the vaccine is inducing HIV tat specific IgA.

In the reverse transcriptase specific IgA response obtained in the SL3261-pHART vaccinated mice over time, the response declined over time. The use of different attenuated bacterial strains for delivering the antigens to the mucosa at each successive dose may eliminate or lessen the decrease in antibody response. There are many attenuated strains of Salmonella that would be so useful. Overall, the results obtained for both the reverse transcriptase and tat vaccines were positive, indicating that measurable levels of antigen specific IgA were produced in the vaccinated mice. The reverse transcriptase vaccine was more effective at inducing higher levels of secretory IgA antibodies.

The helper T cell response specific for the HIV antigens was measured using two different assays. There was a reverse transcriptase specific response developing in these SL3261-pHART vaccinated mice 3 weeks after the first vaccination.

In proliferation assays performed 12 weeks after initial vaccination with the reverse transcriptase vaccine, the responses seen in the splenocytes isolated from the different mice was more pronounced. Four out of the five mice vaccinated with the SL3261 containing the reverse transcriptase construct showed a positive response to the two concentrations of reverse transcriptase antigen used to stimulate the splenocytes. All of the five mice show a positive response to the heat-killed Salmonella used to stimulate the splenocytes. These results indicated that when vaccinated with the live vaccine expressing the HIV reverse transcriptase antigen, these mice developed a helper T cell response specific to the reverse transcriptase. The positive helper T cell response seen in the mice vaccinated with the SL3261-pHART live vaccine indicates, along with the positive results obtained with the reverse transcriptase specific-IgA response, that this method of vaccination is useful The present invention is directed to a model for a live vaccine for HIV by surface expressing specific HIV antigens on an attenuated strain of Salmonella. This vaccine elicited a mucosal IgA response and a helper T cell response specific for the HIV reverse transcriptase antigen. A live vaccine vector, such as the attenuated strain of Salmonella, is easy to administer and does not require special handling or injection. Patients could be fed the doses orally. Secondly, the vaccine is low cost.

In addition to using this method of surface expression for displaying proteins, such as HIV reverse transcriptase and tat, epitopes or peptides could be used for stimulating immunity. In such a construct, the base pair sequence for an immunogenic peptide would follow the lpp-ompA sequence, resulting in surface display of the epitope. This specific epitope, known to stimulate an immune response, would elicit a stronger immunity because of the adjuvant properties of the Salmonella. This method of using just a peptide, as opposed to an entire protein may result in increased bacterial survival and plasmid stability, due to less membrane disruption in the surface expression. An example of such a peptide is an antigenic reverse transcriptase peptide that is known to be a T cell epitope in both humans and C3H/HeJ mice (Hosmalin, 1990).

This technique of surface expressing HIV proteins in the attenuated Salmonella strain SL3261 using an lpp-ompA fusion construct for the construction of live vaccines against HIV can be applied to other viral and bacterial pathogens as well. An example of another virus for which such a vaccine could be developed is the respiratory syncytial virus (RSV), the major cause of hospitalization of infants under the age of one year in the Western world. A useful antigen from RSV is the F protein, which could be surface expressed using this lpp-ompA system in SL3261. This recombinant bacteria could be used as a live vaccine for RSV. Other viral and bacterial vaccines could be developed, by surface expressing pathogen-specific antigens in SL3262, using this lpp-ompA fusion construct.

The following references were cited herein.

Brown, A., et al., *J. of Infectious Diseases* 155 (1): 86–92, (1987).
Levine, M. M., et al., *J. of Clinical Investigation* 79: 888–902, (1987).
Sadoff, J. C., et al., *Science* 240: 336–338, (1988).
Dougan, G., et al., *Advances in Veterinary Science and Comparative Medicine* 33: 271–300, (1989).
Newton, S., et al., *Science* 244: 70–72, (1989).
Fairweather, et al., *Infection and Immunity* 58 (5): 1323–26, (1990).
Franchini, et al., *International Conference on AIDS* 7 (1): 101, (1991).
Charbit, A., et al., *Vaccine* 11 (2): 1221–8, (1993).
Berggren, R. E., et al., *J. of Acquired Immunodeficiency Syndromes and Human Retrovirology* 10: 489–95, (1995).
Haynes, B. F. *Lancet* 348: 933–37, (1996).
Sullivan, N., et al., *J. of Virology* 69 (7): 4413–22, (1995).
Wei, X., et al., *Nature* 373: 117–22, (1995).
Ho, D. D., et al., *Nature* 373: 102, (1995).
Daniel, M. D., et al., *Science* 258: 1938–41, (1992).
Stott, E. J., *Nature* 353: 393, (1991).
Haynes, B. F., *Science* 260: 1279–85, (1993)
Clements, J., et al., *Infection and Immunity* 53 (6): 685–92, (1986).
Service, R. F., et al., *Science* 265: 1522–24, (1995).
Clements, J. D., et al., *Nature Biotechnology* 15: 622–23, (1997).
Staats, H. F., et al., *J. of Immunology* 157: 462–72, (1996).
Charbit, A., et al., *AIDS* 4: 545–551, (1990).
Hale, T. L., et al., *Research in Microbiology* 141: 913–19, (1990).
O' Callaghan, D., et al., *Research in Microbiology* 141: 963–69, (1990).
Tagliabue, et al., *Clinical Experimental Immunology* 62: 242–47, (1985).
Bacon, et al., *British J. of Experimental Pathology* 32: 714–24, (1950).
Germanier, R., et al., *Infectious Immunity* 4: 663–673, (1971).
Germanier, R., et al., *J. of Infectious Diseases* 131: 553–8, 1975).
Hoiseth, S., et al., *Nature* 291: 238–9, 1981).
Curtiss, et al., *Vaccines; New Concepts and Developments:* 261, (1987).
Curtiss III, R., et al., *Infectious Immunity* 55: 3035–43, (1987).
McFarland, W., et al., *Microbial Pathogen* 3:129–41, (1987).

Ohta, M., et al., *Microbiological Immunology* 31: 1259–65, (1987).
Robertsson, J., et al., *Infectious Immunity* 41: 742–50, (1983).
Killar, L. M., et al., *Infectious Immunity* 47: 605–12, (1985).
Emini, E. A., et al., *Journal of Virology* 64: 3647, (1990).
Salk, J., et al., *Science* 260: 1270–72, (1993).
Clerici, M., *J. of the American Medical Association* 271: 42, (1994).
Plummer, F. A., et al., *International Conference on AIDS* 9: 23, (1993).
Kraehenbuhl, et al., *Physiological Reviews* 72 (4): 853–73, (1992).
Curtiss III, R., et al., *Current Topics in Microbiology and Immunology* 146: 35–49, (1989).
Levy, E., et al., *Arb Kaiser Gesundh* 28: 168–71, (1908).
Muller, M., *Centroblatt Bakleriolie Parasitenkunde* 62: 335–73, (1912).
Gaines, S., et al., *J. of Infectious Diseases* 118: 293–306, (1968).
Curtiss III, et al., *The Secretory Immune System* 409: 688, (1983).
Curtiss III, R., et al., *Molecular and Microbiology and Immunology of Streprococcus mutants* p: 173, (1986).
Curtiss III, R., *Current Topics in Microbial Immunology* 118: 253–77, (1985).
Curtiss III, R., *J. of Dental Research* 65: 1034–45, (1986).
Dougan, G., et al., *Infectious Immunity* 52: 344–47, (1986).
Maskell, D., et al, *Vaccines 86: New Approaches to Immunization Developing Vaccines Against Parasitic Bacterial and Viral Diseases* p. 213, (1986).
Cryz Jr., et al., *Infection and Immunity* 63 (4): 1336–39, (1995).
Strugnell, R. A., et al., *Gene* 88: 57–63, (1990).
Levine, M. M., et al., *Research in Microbiology* 141: 807–816, (1990).
Francisco, J. A., et al., *PNAS, USA* 89: 2713–17, (1992).
Sabin, A. B., *PNAS, USA* 89: 8852–55, (1992).
Blazevic, V., et al., *J. of Acquired Immuno deficiency Syndromes* 6: 881–90, (1993).
Li, C. J., et al., *Science* 268: 429–431, (1995).
Walker, B. D., et al., *Science* 240: 64–66, (1988).
Francisco, J. A., et al., *Bio/Technology* 11: 491–5, (1993).
Charles, I., et al., *Trends in Biotechnology* 8: 117–121, (1990).
Clements, J. D., et al., *Infectious Immunity* 46: 564–569, (1984).
Curtiss, R., III, et al., *Vaccine* 6: 155–160, (1988).
Dougan, G., et al., *Semin. Virology*, 1: 29–37, (1990).
Hilleman, M. R., *Antibiotic Chemotherapy* 48: 161–172, (1996).
Hone, D., et al., *Microbial Pathology* 5: 407–418, (1988).
Johnston, M. I., *Hospital Practice:* 125–140, (1997).
Letvin, N. L., *The New England J. of Medicine* 329 (19): 1400–1405, (1993).
Maskell, D., et al., *Microbial Pathology* 2: 211–221, (1987).
O' Callaghan, et al., *FEMS Microbiological Letters* 52: 269–274, (1988).
Poirier, et al., *Journal of Experimental Medicine* 168: 25–32, (1988).
Schultz, A. M., *Advances in Experimental Medicine and Biology* 397: 79–90, (1996).
Stevenson, et al., *FEMS Microbiological Letters* 28: 317–321, (1985)
Stott, E. J., et al., *J. of Antimicrobial Chemotherapy* 37 supp. B: 185–198, (1996).
Tarkka, E., et al., *Microbial Pathology* 6: 327–335, (1989).
Taylor, D. W., et al., *Parasitology* 91: S73–S81, (1986).
Traumont, E. C., et al., *J. of Infectious Diseases* 149: 133–139, (1984).
Whadan, M. H., et al., *J. of Infectious Diseases* 145: 292–96, (1982).
Stover, C. K., et al., *Nature,* 351: 456–60, (1991).
Mukkur, et al., *J. of Medical Microbiology* 24: 11–19, (1987).
Hone, D., et al., *J. of Infectious Diseases* 156: 167–74, (1987).
Clerici, M., et al., *J. of Clinical Investigation* 91 (3): 759–65, (1993).
Dougan, G., et al., *Parasite Immunology* 9: 151–160, (1987).
Dougan, et al., *J. of Infectious Diseases* 158: 1329–1335, (1988).
Hahn, B. H., et al., *PNAS, USA* 82 (14): 4813–7, (1985).
Clavel, F., et al., *Science* 233: 343–6, (1986).
Guyader, M., et al., *Nature* 326: 662–9, (1987).
Rowland-Jones, S., et al., *Nature Medicine* 1 (1): 59–64, (1995).
Clerici, M., et al., *J. of Infectious Diseases* 165: 1012–19, (1992).
De Bruijn, et al., *European J. of Immunology* 25: 1274–85, (1995).
Stryhn, A., et al., *European J. of Immunology* 24: 1404–09, (1994).
Reis e Sousa, et al., *J. of Exper. Medicine* 182: 841–51, (1995).
Kovacsovics-Bankowski, M., et al., *PNAS, USA* 90: 4942–46, (1993).
Harding, C. V., et al., *J. of Immunology* 153: 4925–33, (1994).
Hosmalin, A., et al., *PNAS, USA* 87: 2344–48, (1990).
Stott, E. J., et al., *Archives of Virology* 84: 1–52, (1985)

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of initiating an immune response specific for transactivating protein or reverse transcriptase of human immunodeficiency virus type 1 (HIV-1) in an animal, said method comprises the step of:

administering to said animal an attenuated bacterial host comprising a recombinant plasmid that carries a fusion protein construct, wherein said fusion protein construct comprises a gene required for surface exposure and a gene encoding said transactivating protein or reverse transcriptase of HIV-1, wherein said bacterial host can induce both cellular and humoral anti-HIV-1 immune responses in said animal.

2. The method of claim 1 wherein said immune response comprises a mucosal IgA response and a helper T cell response.

3. The method of claim 1, wherein said attenuated bacterial host is administered orally.

4. The method of claim 1, wherein said attenuated bacterial host is administered in an oral dose of from about $10^{12}$ to about $10^{14}$ CFU.

5. The method of claim 1, wherein said gene required for surface exposure encodes *E. coli* lipoprotein signal sequende linked to a portion of the *E. coli* outer membrane protein ompA.

6. The method of claim 1, wherein said attenuated bacterial host is a strain of *Salmonella typhimurium*, SL3261.

* * * * *

UNITED STATES PATENT AND TRADEMARK OFFICE
CERTIFICATE OF CORRECTION

PATENT NO. : 7,189,402 B2
APPLICATION NO. : 09/244195
DATED : March 13, 2007
INVENTOR(S) : Kitto et al.

It is certified that error appears in the above-identified patent and that said Letters Patent is hereby corrected as shown below:

In claim 2, column 25, line 1, after "claim 1", insert --, --therefor.

Signed and Sealed this

Fifteenth Day of May, 2007

JON W. DUDAS
*Director of the United States Patent and Trademark Office*